(12) United States Patent
Miller et al.

(10) Patent No.: US 8,522,789 B2
(45) Date of Patent: Sep. 3, 2013

(54) AIRWAY DEVICES, TUBE SECURING DEVICES, AND METHODS OF MAKING AND USING THE SAME

(71) Applicant: Ecolab USA Inc., St. Paul, MN (US)

(72) Inventors: Patrick John Miller, Covington, GA (US); Michael D. Hall, Conyers, GA (US); David Alan Daugherty, Columbus, MS (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 13/713,543

(22) Filed: Dec. 13, 2012

(65) Prior Publication Data

US 2013/0098368 A1   Apr. 25, 2013

Related U.S. Application Data

(60) Division of application No. 12/390,771, filed on Feb. 23, 2009, now Pat. No. 8,356,597, which is a continuation-in-part of application No. 12/104,075, filed on Apr. 16, 2008.

(60) Provisional application No. 60/923,548, filed on Apr. 16, 2007.

(51) Int. Cl.
*A62B 18/08* (2006.01)

(52) U.S. Cl.
USPC ............. 128/207.17; 128/207.14; 128/207.15

(58) Field of Classification Search
USPC .............. 128/207.11, 207.14, 207.15, 207.17
See application file for complete search history.

(56) References Cited

U.S. PATENT DOCUMENTS

| | | | | |
|---|---|---|---|---|
| 3,946,742 | A * | 3/1976 | Eross | 128/207.17 |
| 5,490,504 | A * | 2/1996 | Vrona et al. | 128/207.17 |
| 6,196,224 | B1 * | 3/2001 | Alfery | 128/207.14 |
| 6,755,191 | B2 * | 6/2004 | Bertoch et al. | 128/200.26 |

* cited by examiner

*Primary Examiner* — Glenn Richman
(74) *Attorney, Agent, or Firm* — Andrew D. Sorensen; Amy J. Hoffman

(57) ABSTRACT

Airway devices and tube securing devices are disclosed. Methods of making and using airway devices and tube securing devices are also disclosed.

8 Claims, 13 Drawing Sheets

AIRWAY DEVICES, TUBE SECURING DEVICES, AND METHODS OF MAKING AND USING THE SAME

CROSS-REFERENCE TO RELATED APPLICATIONS

This patent application is a divisional application of (i) application Ser. No. 12/390,771 filed on Feb. 23, 2009 and entitled "AIRWAY DEVICES, TUBE SECURING DEVICES, AND METHODS OF MAKING AND USING THE SAME", now U.S. Pat. No. 8,356,597, which claims the benefit of priority to (ii) U.S. Provisional Patent Application Ser. No. 60/923,548 filed on Apr. 16, 2007 and entitled "SUPRAGLOTTIC AIRWAY LARYNGOPHARYNGEAL TUBE" and (iii) U.S. patent application Ser. No. 12/104,075 filed on Apr. 16, 2008 and entitled "AIRWAY DEVICES AND METHODS OF MAKING AND USING THE SAME"; (iv) U.S. patent application Ser. No. 12/907,794 filed on Oct. 19, 2010 and entitled "AIRWAY DEVICES, TUBE SECURING DEVICES, AND METHODS OF MAKING AND USING THE SAME", all of which are hereby incorporated by reference in their entirety.

TECHNICAL FIELD

The present invention relates to airway devices including devices referred to as supraglottic airway laryngopharyngeal tubes (SALTs) or oropharyngeal airway tubes. The present invention also relates to tube securing devices that may be used in combination with an endotracheal tube to secure a position of the endotracheal tube within an airway device. The present invention further relates to methods of making and using airway devices and tube securing devices.

BACKGROUND OF THE INVENTION

Oropharyngeal airways are designed to provide an airway for patients who are unconscious or comatose and are unable to maintain an airway on their own because of an unintact gag reflex. An oropharyngeal airway is inserted into the patient's oropharynx and restrains the tongue from retracting and occluding the glottic opening.

The traditional procedure of endotracheal intubation is typically accomplished in an emergency setting by visualizing the glottic opening with the utilization of a laryngoscope, and then advancing an endotracheal tube through the glottic opening. In the emergency setting, obstacles such as vomitus, blood, or patient positioning can make visualization of the glottic opening extremely difficult if not impossible. Even when aggressive oropharyngeal suctioning is applied, visualization of the glottic opening often fails to be accomplished. If a patient's airway cannot be rapidly and effectively secured, the patient will become hypoxic, which results in rapid deterioration of the patient's health and often results in death.

Given the need for quick action and the difficulty, in some cases, of being able to visually detect the glottic opening of a patient, a number of devices have been developed that do not require visualization of the glottic opening. Such devices have existed for years, but still suffer from one or more drawbacks. For example, the tracheal guide disclosed in U.S. Pat. No. 5,720,275 comprises a distal end in the form of a shovel-like tongue (25) and ears (18,33) positioned along opposite sides of a U-shaped passage (17). In order to operate correctly, the disclosed tracheal guide must be precisely positioned within a patient so that ears (18,33) extend into the piriform fossa (19,34) of the patient, the piriform fossa (19, 34) being located in the vicinity of the glottic opening (39) as shown in FIGS. 1-4. In many emergency situations, such precise positioning is not practical given the state of the patient and the need to act quickly.

Further, once a tracheal guide is properly positioned, an endotracheal tube is inserted through the tracheal guide and guided into the trachea of the patient. Once the endotracheal tube is properly positioned, an air source is connected to the endotracheal tube so that air may be administered to the patient.

What is needed in the art is a simple airway device that is (1) capable of quickly aligning certain anatomical structures of a patient's airway so as to provide a guided pathway for an endotracheal tube to be inserted through the device and guided into the trachea of the patient, and (2) can be inserted into a patient without the need for precise positioning of device components/features. What is also needed in the art is a simple tube securing device that is capable of securing a portion of an endotracheal tube extending from a patient's mouth to prevent undesirable movement of the endotracheal tube extending from the patient's mouth.

SUMMARY OF THE INVENTION

The present invention is directed to airway devices that are capable of quickly aligning certain anatomical structures of a patient's airway so as to provide a guided pathway for an endotracheal tube to be inserted through the device and guided into the trachea of the patient. The disclosed devices can be inserted into a patient without the need for precise positioning of device components/features during insertion of the device.

In one exemplary embodiment, the present invention is directed to an airway device comprising a tubular member having a proximal end, a distal end opposite the proximal end, a tubular conduit positioned between the proximal end and the distal end, and a channel extending from a first channel opening at the proximal end through the tubular conduit to a second channel opening proximate the distal end. In this exemplary embodiment, the distal end of the device has an overall distal end width bound by opposing side walls, an overall distal end height bound by an uppermost distal end surface and a lower distal end surface, and a tear-drop shape represented by the uppermost distal end surface, the lower distal end surface, and a curved distal end surface connecting the uppermost distal end surface to the lower distal end surface, wherein the curved distal end surface extends substantially perpendicular to and between the opposing side walls. The tear-drop shape and outer dimensions of the device enable quick insertion of the device into a patient's mouth until the curved distal end surface of the device abuts corniculate cartilage of the patient.

In a further exemplary embodiment, the present invention is directed to an airway device comprising a tubular member having a proximal end, a distal end opposite the proximal end, a tubular conduit positioned between the proximal end and the distal end, and a channel extending from a first channel opening at the proximal end through the tubular conduit to a second channel opening proximate the distal end; and an epiglottis guard extending along an upper portion of the tubular member. In this exemplary embodiment, the epiglottis guard comprises (i) a first end that is connected to the tubular member proximate the second channel opening, (ii) a second end that is not connected to the tubular member and is positioned between the second channel opening and the distal end, and (iii) opposing edges extending from the first end to the second end, wherein the opposing edges are not connected to the tubular member. In this exemplary embodiment, the second end of the epiglottis guard is operatively adapted to move into or away from the channel, for example, during insertion of an endotracheal tube through the channel of the device and into a patient's trachea.

The present invention is also directed to tube securing devices that are capable of securing an endotracheal tube to a patient. In one exemplary embodiment, the tube securing device comprises a tube securing device for stabilizing a position of an endotracheal tube on a patient, wherein the tube securing device comprises (i) an endotracheal tube clamping member operatively adapted to clamp onto an outer surface of an endotracheal tube, the endotracheal tube clamping member comprising at least one clamp connector positioned along an outer surface of the endotracheal tube clamping member; and (ii) a strap comprising one or more strap connectors positioned along a length of the strap, each of the one or more strap connectors being independently connectable to a corresponding clamp connector.

In another exemplary embodiment, the tube securing device comprises a tube securing device for stabilizing a position of an endotracheal tube extending from a patient's mouth, wherein the tube securing device comprises (1) an endotracheal tube clamping member operatively adapted to clamp onto an outer surface of an endotracheal tube, the endotracheal tube clamping member comprising (i) a closed end having a closed end inner surface and a closed end outer surface, (ii) an open end opposite the closed end and comprising (iii) a pawling member and (iv) a ratcheting member, the pawling member being movable along a row of ratcheting teeth along the ratcheting member so as to lock the pawling member within the ratcheting member and simultaneously clamp onto the outer surface of the endotracheal tube, and (v) a pair of clamp connectors positioned along opposite sides of the closed end outer surface, wherein each of the clamp connectors comprises a mushroom-shaped member extending outward from opposite sides of the closed end outer surface; and (2) a strap comprising (i) a strip of material having opposite strip ends, a strip width, and a strip length extending between the opposite strip ends, and (ii) a plurality of strap connectors positioned along the strip length, each of the one or more strap connectors being independently connectable to a corresponding clamp connector, wherein each strap connector comprises an opening extending through the strap. In this exemplary embodiment, the strap length enables the strap to extend from the patient's mouth, along a rear portion of the patient's head or neck region, and back to the patient's mouth so as to surround a portion of the patient's head.

The present invention is further directed to methods of making airway devices and tube securing devices suitable for use in an endotracheal intubation procedure. In one exemplary embodiment, the present invention is directed to a method of making an airway device comprising forming a tubular member having a proximal end, a distal end opposite the proximal end, a tubular conduit positioned between the proximal end and the distal end, and a channel extending from a first channel opening at the proximal end through the tubular conduit to a second channel opening proximate the distal end, wherein the distal end of the device has an overall distal end width bound by opposing side walls, an overall distal end height bound by an uppermost distal end surface and a lower distal end surface, and a tear-drop shape represented by the uppermost distal end surface, the lower distal end surface, and a curved distal end surface connecting the uppermost distal end surface to the lower distal end surface, wherein the curved distal end surface extends substantially perpendicular to and between the opposing side walls. In this exemplary embodiment, the forming step may comprise a single thermoforming step (e.g., a single molding step) or may comprise a single thermoforming step in combination with other possible method steps.

In a further exemplary embodiment, the present invention is directed to a method of making an airway device comprising forming a tubular member having a proximal end, a distal end opposite the proximal end, a tubular conduit positioned between the proximal end and the distal end, a channel extending from a first channel opening at the proximal end through the tubular conduit to a second channel opening proximate the distal end, and an epiglottis guard extending along an upper portion of the tubular member. In this exemplary embodiment, the forming step may comprise a single thermoforming step (e.g., a single molding step) or may comprise a thermoforming step (e.g., for forming the tubular member) in combination with one or more other method steps. For example, the epiglottis guard may be formed by cutting an upper portion of the tubular member extending over the channel so as to form an epiglottis guard comprising (i) a first end that is connected to the tubular member proximate the second channel opening, (ii) a second end that is not connected to the tubular member and is positioned between the second channel opening and the distal end, and (iii) opposing cut edges extending from the second end to the first end, wherein the second end of the epiglottis guard is operatively adapted to move into or away from the channel, for example, during insertion of an endotracheal tube through the channel of the device and into a patient's trachea.

The present invention is also directed to methods of making a tube securing device. In one exemplary embodiment, the method of making a tube securing device comprises (i) forming an endotracheal tube clamping member operatively adapted to clamp onto an outer surface of an endotracheal tube, the endotracheal tube clamping member comprising at least one clamp connector positioned along an outer surface of the endotracheal tube clamping member; and (ii) forming a strap comprising one or more strap connectors positioned along a length of the strap, each of the one or more strap connectors are independently connectable to a corresponding clamp connector. In this exemplary embodiment, each forming step may comprise independent thermoforming steps (e.g., a molding step for forming the endotracheal tube clamping member and an extrusion step for forming the strap).

The present invention is even further directed to methods of using airway devices and tube securing devices in an endotracheal intubation procedure. In one exemplary embodiment, the present invention is directed to a method of inserting an endotracheal tube into a trachea of a patient comprising the steps of inserting an airway device into the patient's mouth until a curved distal end surface of the device abuts corniculate cartilage of the patient, the device comprising a tubular member having a proximal end, a distal end opposite the proximal end, a tubular conduit positioned between the proximal end and the distal end, and a channel extending from a first channel opening at the proximal end through the tubular conduit to a second channel opening proximate the distal end, wherein the distal end has an overall distal end width bound by opposing side walls, an overall distal end height bound by an uppermost distal end surface and a lower distal end surface, and a tear-drop shape represented by the uppermost distal end surface, the lower distal end surface, and the curved distal end surface connecting the uppermost distal end surface to the lower distal end surface, the curved distal end surface extending substantially perpendicular to and between the opposing side walls; and pushing an endotracheal tube through the channel of the device. This exemplary method may comprise one or more additional steps including, but not limited to, connecting a ventilation mask to the proximate end of the device after the inserting step, disconnecting the ventilation mask from the proximate end of the device after the connecting step and prior to said pushing step, coating at least a portion of a leading end of the endotracheal tube with a lubricant prior to the pushing step, and securing a portion of the endotracheal tube extending from the patient's mouth to the patient via a tube securing device comprising an endotracheal tube clamping member and a strap that connects to the endotracheal tube clamping member and extends around a portion of the patient's head.

The present invention is even further directed to kits suitable for performing an endotracheal intubation procedure. In one exemplary embodiment, the kit comprises (i) at least one of the disclosed airway devices in combination with (ii) an endotracheal tube. In another exemplary embodiment, the kit comprises (i) at least one of the disclosed airway devices in combination with (ii) a tube securing device comprising an endotracheal tube clamping member and a strap that is connectable to the endotracheal tube clamping member and extendable around a portion of a patient's head. In a further exemplary embodiment, the kit comprises (i) a tube securing device comprising an endotracheal tube clamping member and a strap that is connectable to the endotracheal tube clamping member and extendable around a portion of a patient's head in combination with (ii) an endotracheal tube. In yet another exemplary embodiment, the kit comprises (i) at least one of the disclosed airway devices in combination with (ii) an endotracheal tube, (iii) an endotracheal tube clamping member and (iv) a strap that is connectable to the endotracheal tube clamping member and extendable around a portion of a patient's head. Each of the kits of the present invention may further comprise additional kit components including, but not limited to, a lubricant, and a ventilation mask.

In one exemplary embodiment, the kit of the present invention comprises (1) a tube securing device for stabilizing a position of an endotracheal tube on a patient, wherein the tube securing device comprises (i) an endotracheal tube clamping member operatively adapted to clamp onto an outer surface of an endotracheal tube, the endotracheal tube clamping member comprising at least one clamp connector positioned along an outer surface of the endotracheal tube clamping member; and (ii) a strap comprising one or more strap connectors positioned along a length of the strap, each of the one or more strap connectors being independently connectable to a corresponding clamp connector; and (2) an airway device, wherein the airway device comprises (a) a tubular member having a proximal end, a distal end opposite the proximal end, a tubular conduit positioned between the proximal end and the distal end, and a channel extending from a first channel opening at the proximal end through the tubular conduit to a second channel opening proximate the distal end; and (b) an epiglottis guard extending along an upper portion of the tubular member, the epiglottis guard comprising (i) a first end that is connected to the tubular member proximate the second channel opening, (ii) a second end that is not connected to the tubular member and positioned between the second channel opening and the distal end, and (iii) opposing edges extending from the first end to the second end, the opposing edges being not connected to the tubular member, wherein the second end is operatively adapted to move into or away from the channel.

These and other features and advantages of the present invention will become apparent after a review of the following detailed description of the disclosed embodiments and the appended claims.

BRIEF DESCRIPTION OF THE DRAWINGS

The present invention is further described with reference to the appended figures, wherein.

DETAILED DESCRIPTION OF THE INVENTION

The present invention is directed to airway devices suitable for use in an endotracheal intubation procedure. As used herein, the phrase "airway device" or "airway devices" is used to describe a class of devices that includes, but is not limited to, supraglottic airway laryngopharyngeal tubes (SALTs) and oropharyngeal airway tubes. In particular, the disclosed airway devices are suitable for use in procedures for providing ventilation (e.g., air) to a patient, procedures for inserting an endotracheal tube into the trachea of a patient, or both. The present invention is further directed to methods of making airway devices, as well as methods of using airway devices in an endotracheal intubation procedure. One exemplary airway device of the present invention suitable for use in an endotracheal intubation procedure is shown as exemplary airway device 50 in FIG. 1.

Figure 1:
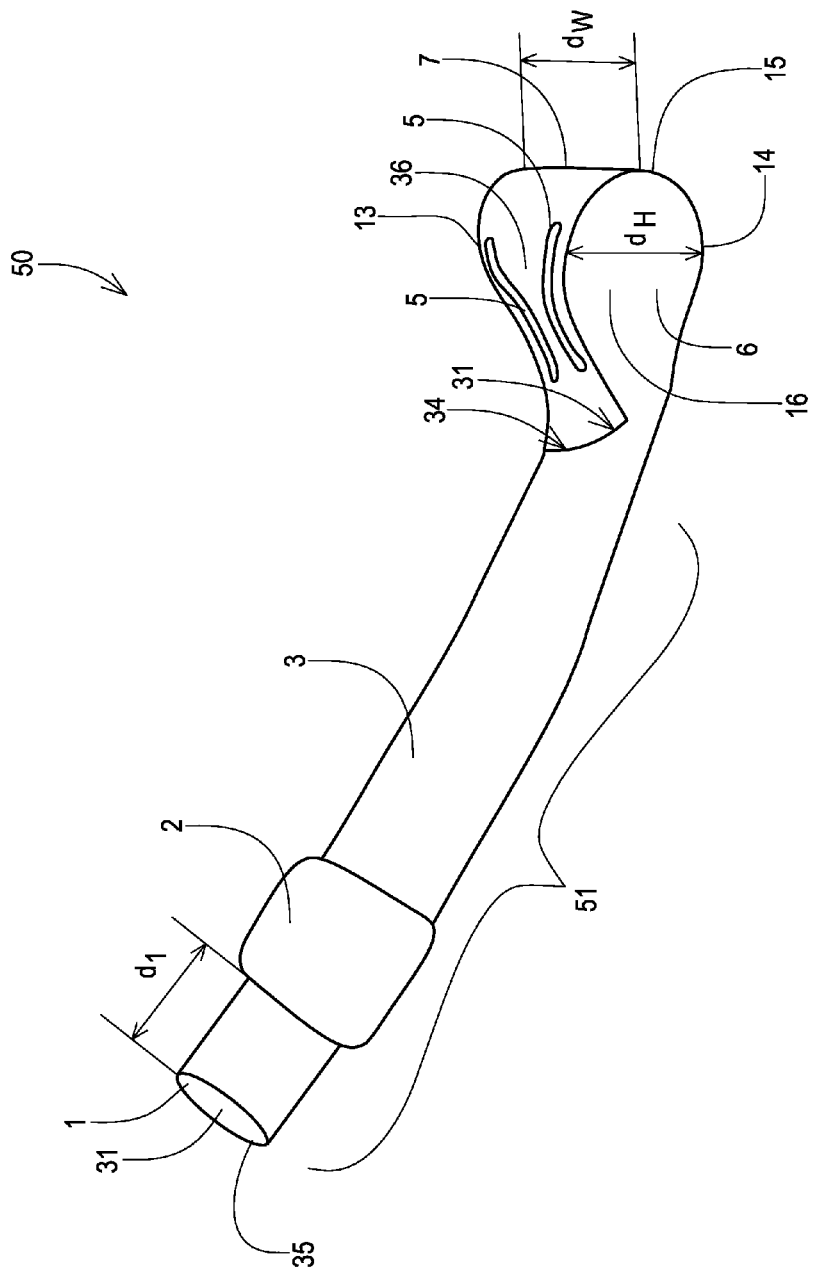
FIG. 1 provides a perspective view of an exemplary airway device of the present invention.

Referring to FIG. 1, exemplary airway device 50 comprises a tubular member 51 having a proximal end 1, a distal end 6 opposite proximal end 1, a tubular conduit 3 positioned between proximal end 1 and distal end 6, and a channel 31 extending from a first channel opening 35 at proximal end 1 through tubular conduit 3 to a second channel opening 34 proximate distal end 6. Exemplary airway device 50 further comprises a depth indicator ring 2 proximate proximal end 1. Although shown positioned a distance $d_1$ from proximal end 1, it should be understood that depth indicator ring 2 may be positioned at proximal end 1 (i.e., $d_1=0$) or any distance $d_1$ from proximal end 1. Typically, depth indicator ring 2 has an outer diameter that is greater than an outer diameter of tubular conduit 3 as shown in FIG. 1. As discussed further below, depth indicator ring 2 may be used to signal a proper depth of insertion into a patient's mouth during an endotracheal intubation procedure.

As shown in FIG. 1, distal end 6 of exemplary airway device 50 has an overall distal end width, $d_W$, bound by opposing side walls 16 and 17 (see, FIG. 3), an overall distal end height, $d_H$, bound by an uppermost distal end surface 13 and a lower distal end surface 14, and a tear-drop shape represented by uppermost distal end surface 13, lower distal end surface 14, and a curved distal end surface 15 connecting uppermost distal end surface 13 to lower distal end surface 14. As shown in FIG. 1, curved distal end surface 15 extends substantially perpendicular to and between opposing side walls 16 and 17. In one desired embodiment, at least a portion of each of opposing side walls 16 and 17 (see, FIG. 3) proximate curved distal end surface 15 extends substantially parallel to one another so as to form right angles with curved distal end surface 15. As discussed further below (and shown in FIG. 5), the tear-drop shape and outer dimensions of exemplary airway device 50 enable quick insertion of exemplary airway device 50 into a patient's mouth until curved distal end surface 15 of exemplary airway device 50 abuts corniculate cartilage of a patient.

In some exemplary embodiments, the airway devices of the present invention further comprise a pair of raised ridges that form a channel extension operatively adapted to direct an endotracheal tube along an uppermost distal end surface of the device toward a glottic opening of a patient. As shown in FIG. 1, exemplary airway device 50 comprises raised ridges 5 extending along uppermost distal end surface 13 between second channel opening 34 and a tip portion 7 of distal end 6. Raised ridges 5 form a channel extension 36 that is operatively adapted to direct an endotracheal tube (not shown) along uppermost distal end surface 13 toward a glottic opening of a patient (see, FIGS. 4-5).

Desirably, raised ridges 5 are mirror images of one another. In other words, a line dissecting channel extension 36 would be equally spaced from corresponding points along each of raised ridges 5. In some embodiments, raised ridges 5 are substantially parallel with one another. In other embodiments, such as shown in FIG. 1, raised ridges 5 have some curvature therein. For example, raised ridges 5 may be configured such that a shortest distance between raised ridges 5 is along a center portion of a given raised ridge 5 or along a portion of a given raised ridge 5 proximate second channel opening 34 while a greatest distance between raised ridges 5 is along a portion of a given raised ridge 5 proximate tip portion 7 of distal end 6 (see, for example, raised ridge 5 shown in FIG. 3).

Figure 2:
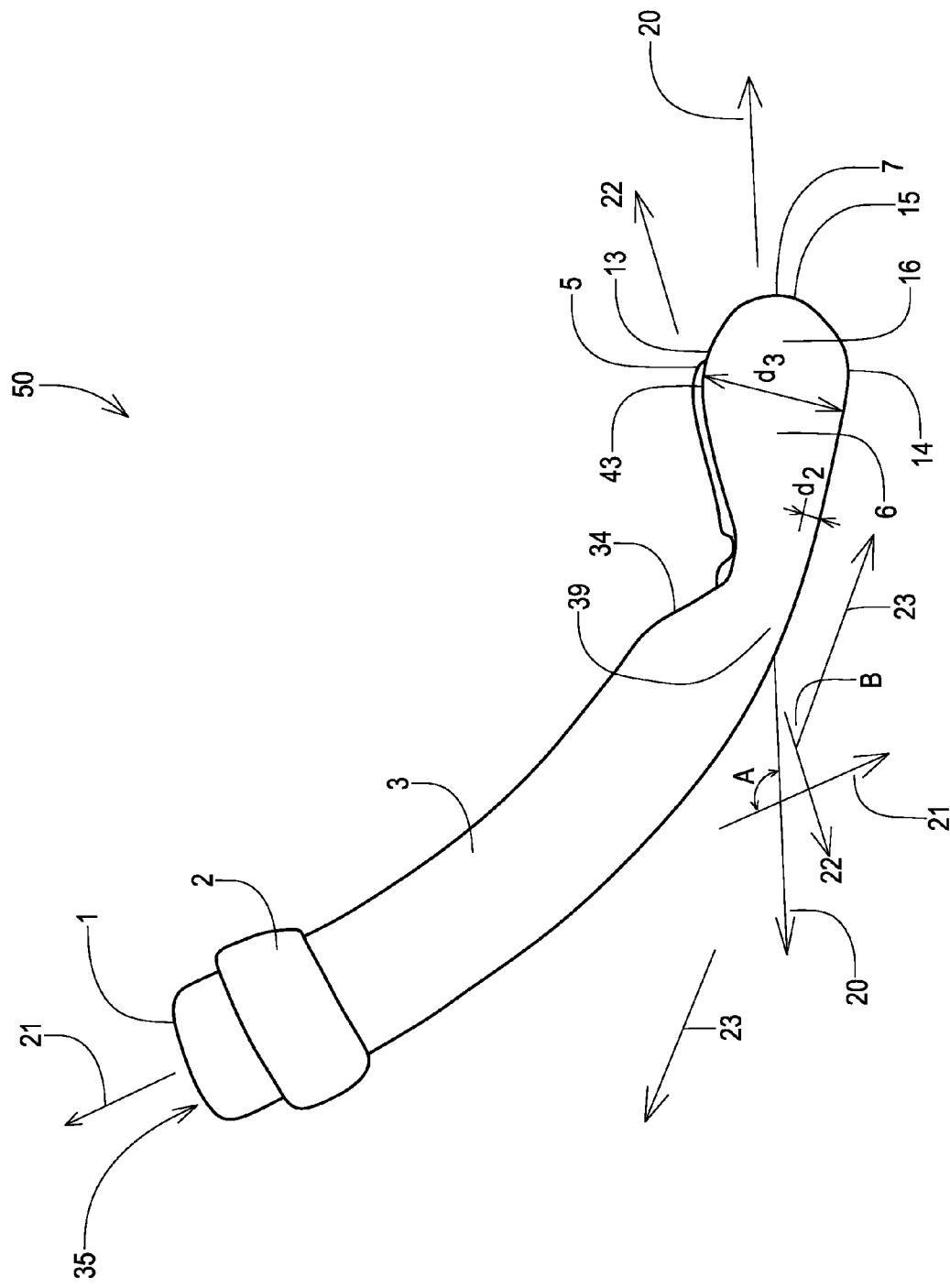
FIG. 2 provides a side view of the exemplary airway device shown in FIG. 1.

As shown in FIG. 2, exemplary airway device 50 has a curved configuration. The curved configuration may be further described with reference to lines 20-20 and 21-21, as well as angle A (also referred to herein as the "angle of curvature") formed therebetween. In one desired embodiment, tubular member 51 has a curved section between proximal end 1 and distal end 6 such that (i) a first line 21-21 extending substantially parallel to tubular member 51 out of first channel opening 35 (i.e., dissects first channel opening 35) and (ii) a second line 20-20 extending from distal end 6 through curved distal end surface 15 and positioned an equal distance from uppermost distal end surface 13 and lower distal end surface 14 forms an angle A with one another of less than 180°. Typically, angle A ranges from about 110° to about 165°, more typically, from about 130° to about 145°, and in one exemplary embodiment, about 135°.

Further, as shown in FIG. 2, distal end 6 of exemplary airway device 50 desirably provides an upward surface inclination from a lowest point within second channel opening 34 to a point along uppermost distal end surface 13. In one desired embodiment, channel 31 has a lowest channel point 39 along channel 31, wherein lowest channel point 39 is a first distance $d_2$ above lower distal end surface 14, and channel extension 36 has a highest channel extension point 43 along uppermost distal end surface 13, wherein highest channel extension point 43 is a second distance $d_3$ above lower distal end surface 14, wherein second distance $d_3$ is greater than first distance $d_2$. Desirably, highest channel extension point 43 comprises an uppermost point along uppermost distal end surface 13.

This surface inclination feature of exemplary airway device 50 may be further described with reference to lines 22-22 and 23-23, as well as angle B (also referred to herein as the "angle of inclination") formed therebetween. In one desired embodiment, distal end 6 of exemplary airway device 50 provides an upward surface inclination such that (i) first line 23-23 extending substantially parallel to lower distal end surface 14 and (ii) line 22-22 extending through lowest channel point 39 and along uppermost distal end surface 13 forms an angle B with one another of greater than about 10°. Typically, angle B ranges from about 10° to about 60°, more typically, from about 25° to about 50°, and in one exemplary embodiment, about 30° to about 40°.

Figure 3:
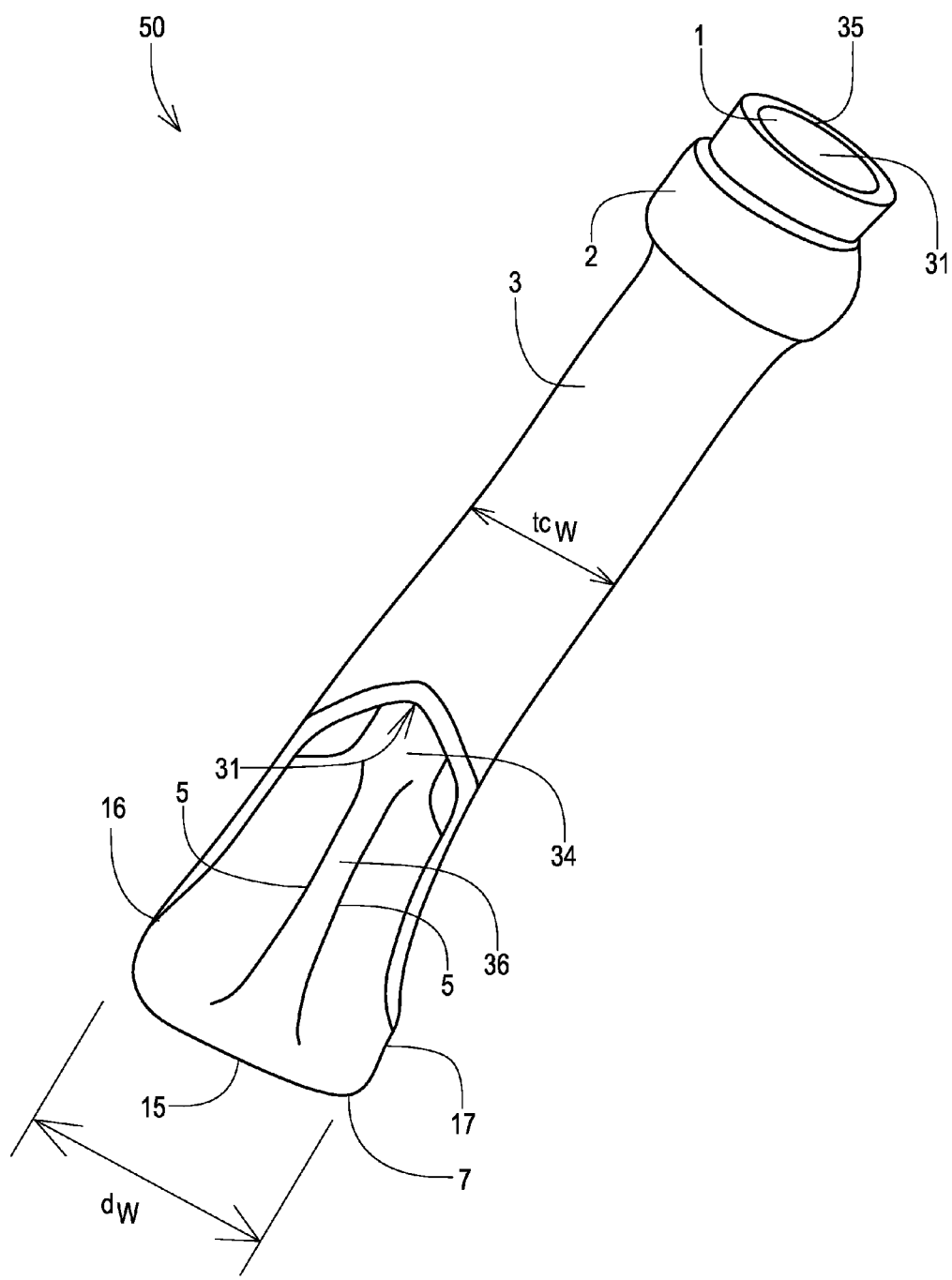
FIG. 3 provides a top view of the exemplary airway device shown in FIG. 1.

FIG. 3 provides a top view of exemplary airway device 50. In FIG. 3, channel 31, first channel opening 35, second channel opening 34, raised ridges 5, channel extension 36, and opposing side walls 16 and 17 are more depicted. As shown in FIG. 3, overall distal end width $d_W$ is typically greater than an overall width $tc_W$ of tubular conduit 3. As discussed further below, overall distal end width $d_W$ functions to seat exemplary airway device 50 against corniculate cartilage of a patient when positioned within the patient's oropharnyx without any portion of exemplary airway device 50 extending into the esophagus or piriform fossa of the patient.

Figure 4:
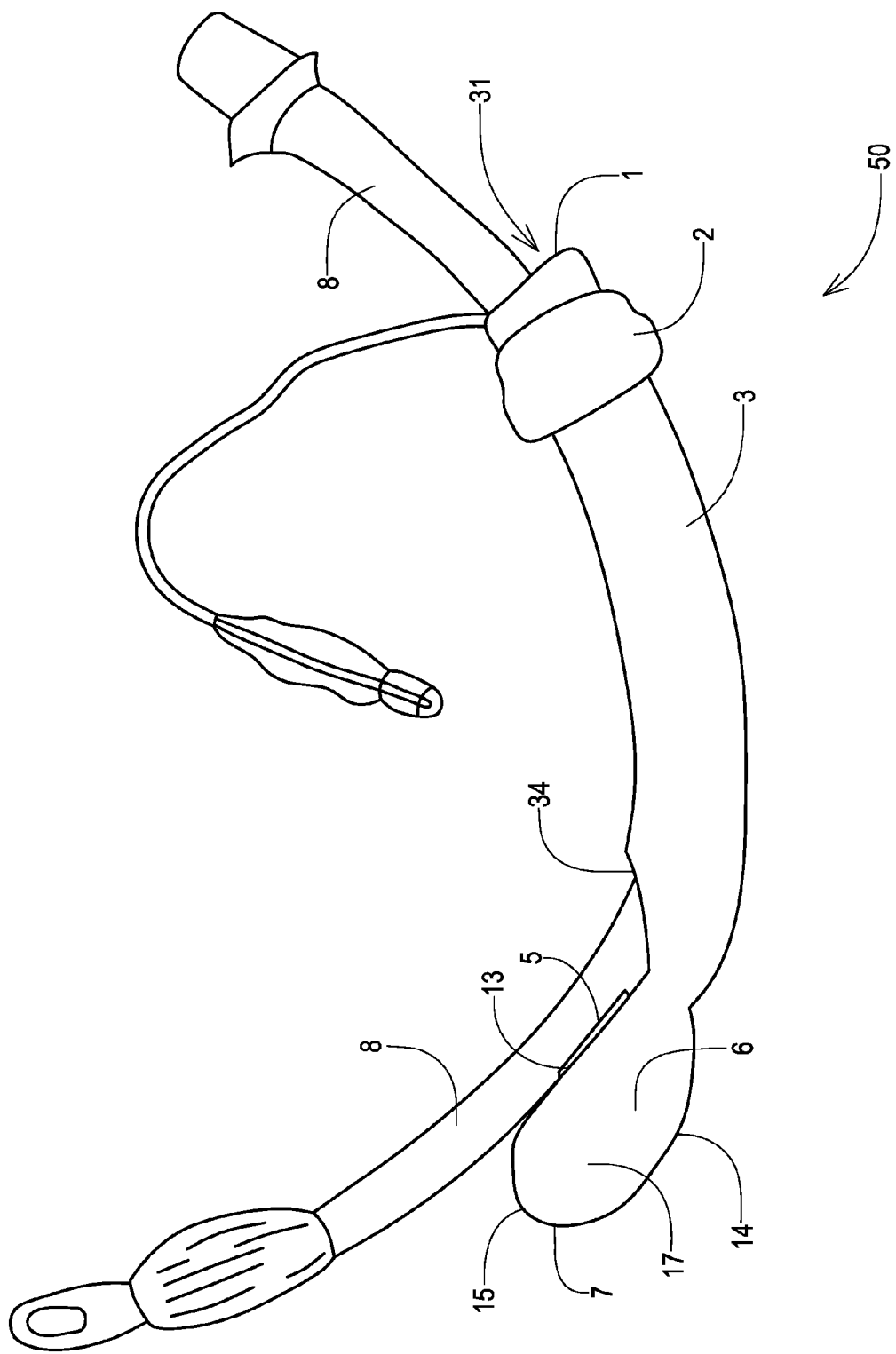
FIG. 4 provides a side view of the exemplary airway device shown in FIG. 1 with an endotracheal tube inserted through the exemplary airway device.
Figure 5:
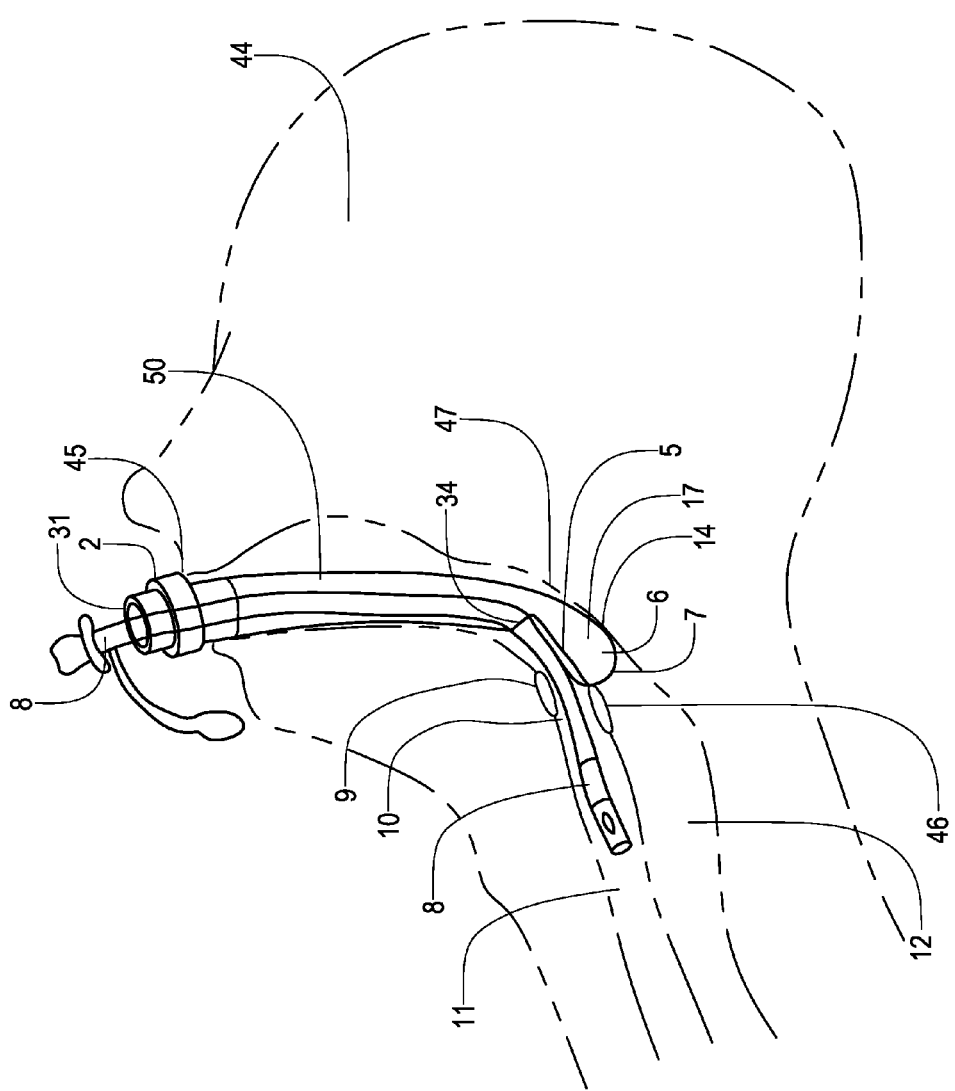
FIG. 5 provides a view of the exemplary airway device shown in FIG. 1 positioned within a patient during an endotracheal intubation procedure.

Exemplary airway device 50 may be used in combination with an endotracheal tube during an endotracheal intubation procedure. FIG. 4 provides a side view of exemplary airway device 50 in combination with an endotracheal tube 8 inserted through channel 31 of exemplary airway device 50. As shown in FIG. 4, endotracheal tube 8 extends through channel 31 of exemplary airway device 50, out of second channel opening 34 and along channel extension 36 between raised ridges 5 along uppermost distal end surface 13. FIG. 5 provides a view of exemplary airway device 50 in combination with endotracheal tube 8 as positioned within a patient 44 during an endotracheal intubation procedure.

As shown in FIG. 5, exemplary airway device 50 extends from out of mouth 45 of patient 44 to corniculate cartilage 46 proximate the opening into the esophagus 12 of patient 44. Distal end tip 7 of distal end 6 abuts corniculate cartilage 46 so as to position second channel opening 34 proximate glottic opening 10 leading into the trachea 11 of patient 44. Overall distal end height, $d_H$, of distal end 6 prevents exemplary airway device 50 from extending beyond corniculate cartilage 46 and into esophagus 12. (Note that lower distal end surface 14 is in contact with throat wall 47 so as to lodge distal end 6 against corniculate cartilage 46.) Endotracheal tube 8 extends through channel 31 of exemplary airway device 50, out of second channel opening 34, along channel extension 36 between raised ridges 5 and along uppermost distal end surface 13, through glottic opening 10 and into trachea 11 of patient 44.

Figure 6:
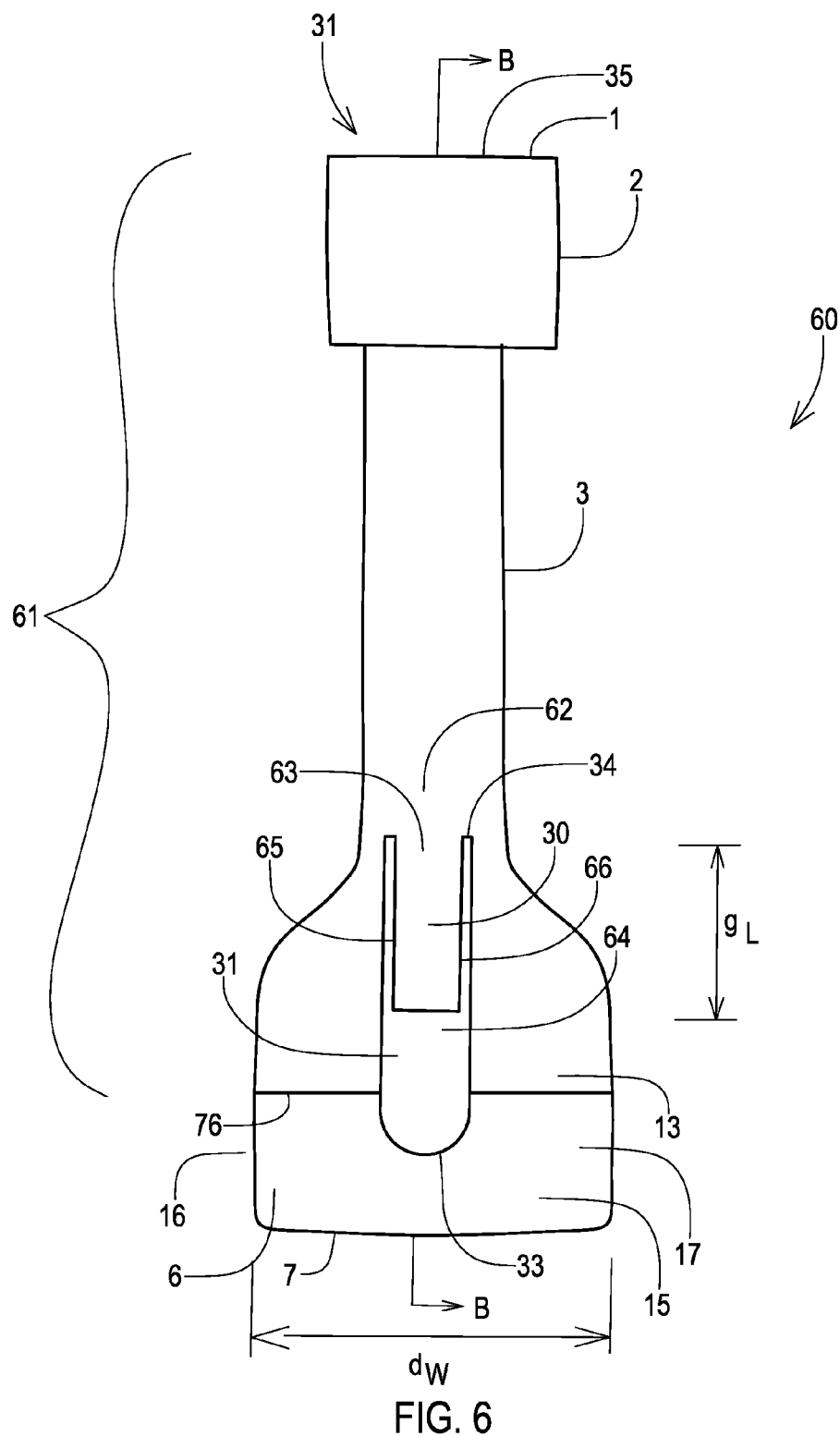
FIG. 6 provides a top view of another exemplary airway device of the present invention.
Figure 8:
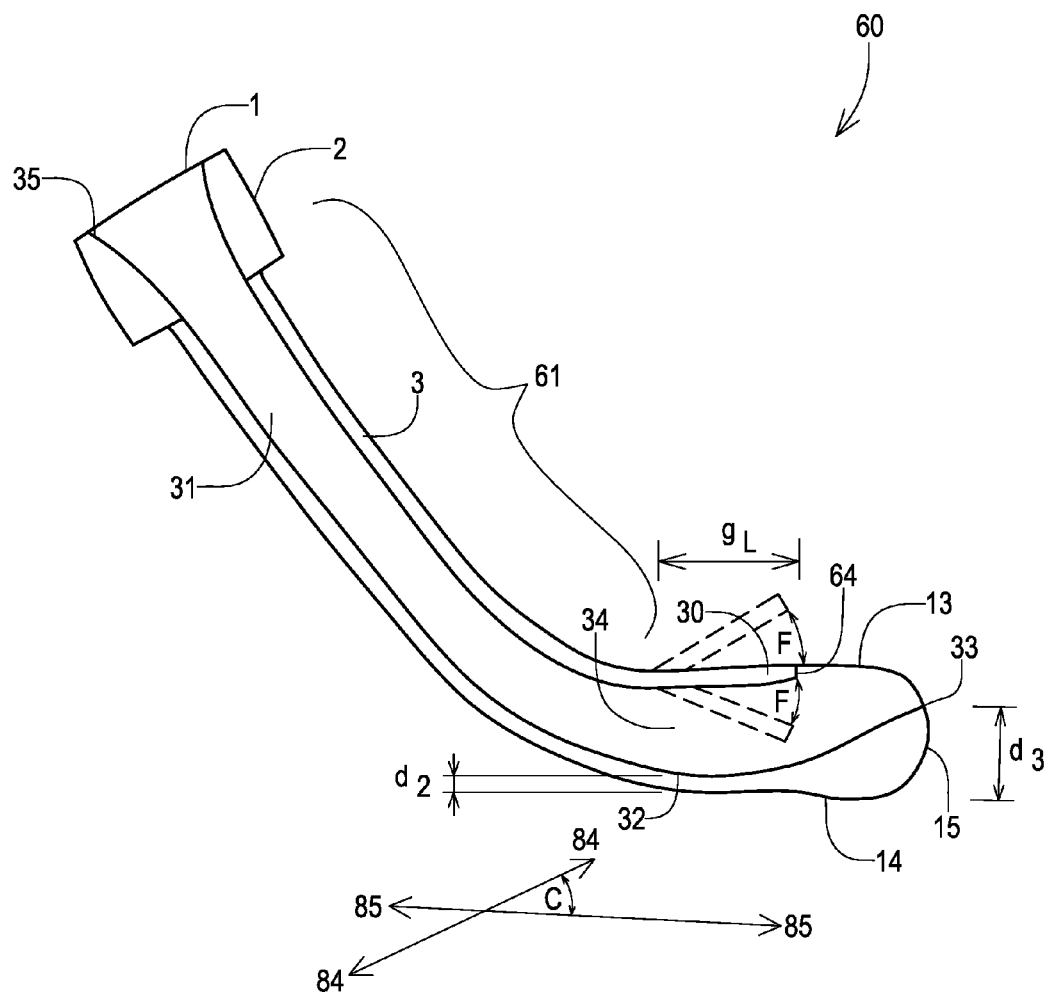
FIG. 8 provides a cross-sectional view of the exemplary airway device shown in FIG. 6 along line B-B shown in FIG. 6.

FIG. 6 provides a top view of another exemplary airway device 60 of the present invention. As shown in FIG. 6, exemplary airway device 60 comprises tubular member 61 having a proximal end 1, a distal end 6 opposite proximal end 1, a tubular conduit 3 positioned between proximal end 1 and distal end 6, and a channel 31 extending from a first channel opening 35 at proximal end 1 through tubular conduit 3 to a second channel opening 34 proximate distal end 6. Exemplary airway device 60 further comprises an epiglottis guard 30 extending along an upper portion 62 of tubular member 61, wherein epiglottis guard 30 comprises (i) a first end 63 that is connected to tubular member 61 proximate second channel opening 34, (ii) a second end 64 that is not connected to tubular member 61 and is positioned between second channel opening 34 and distal end 6, and (iii) opposing edges 65 and 66 extending from first end 63 to second end 64, wherein opposing edges 65 and 66 are not connected to tubular member 61, and second end 64 is operatively adapted to move into or away from channel 31 (see, for example, possible movement of second end 64 as shown in FIG. 8).

Epiglottis guard 30 has a guard length, $g_L$, extending the length of opposing edges 65 and 66. Guard length, $g_L$, may vary as desired, but typically guard length, $g_L$, extends a distance that is less than or equal to a distance from proximate second channel opening 34 to an end point 33 of channel 31. More typically, guard length, $g_L$, extends a distance that is about half the distance from proximate second channel opening 34 to end point 33 of channel 31. In dimensions, guard length, $g_L$, typically ranges from about 1.3 centimeters (cm) (0.5 inches (in)) to about 3.8 cm (1.5 in) in length.

Figure 7:
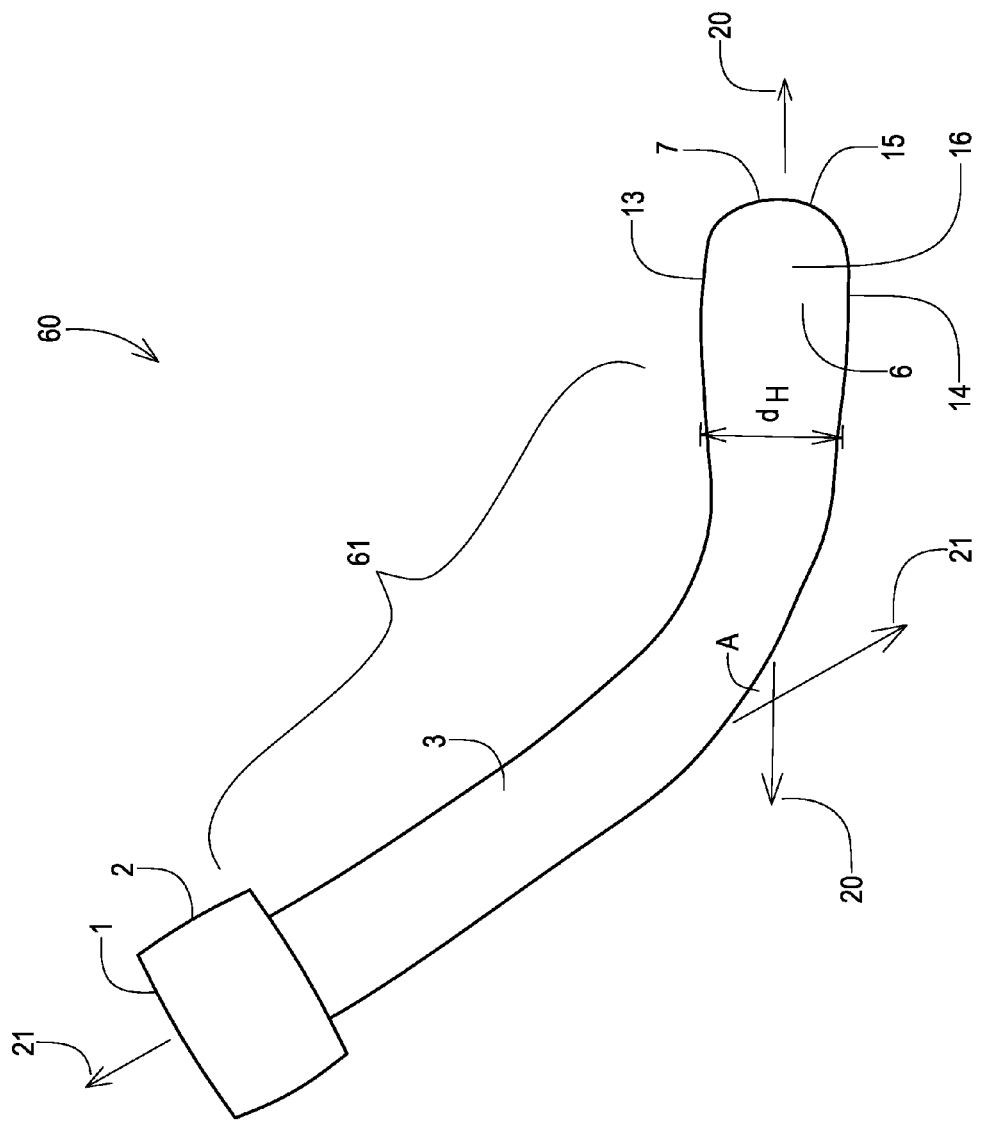
FIG. 7 provides a side view of the exemplary airway device shown in FIG. 6.
Figure 10:
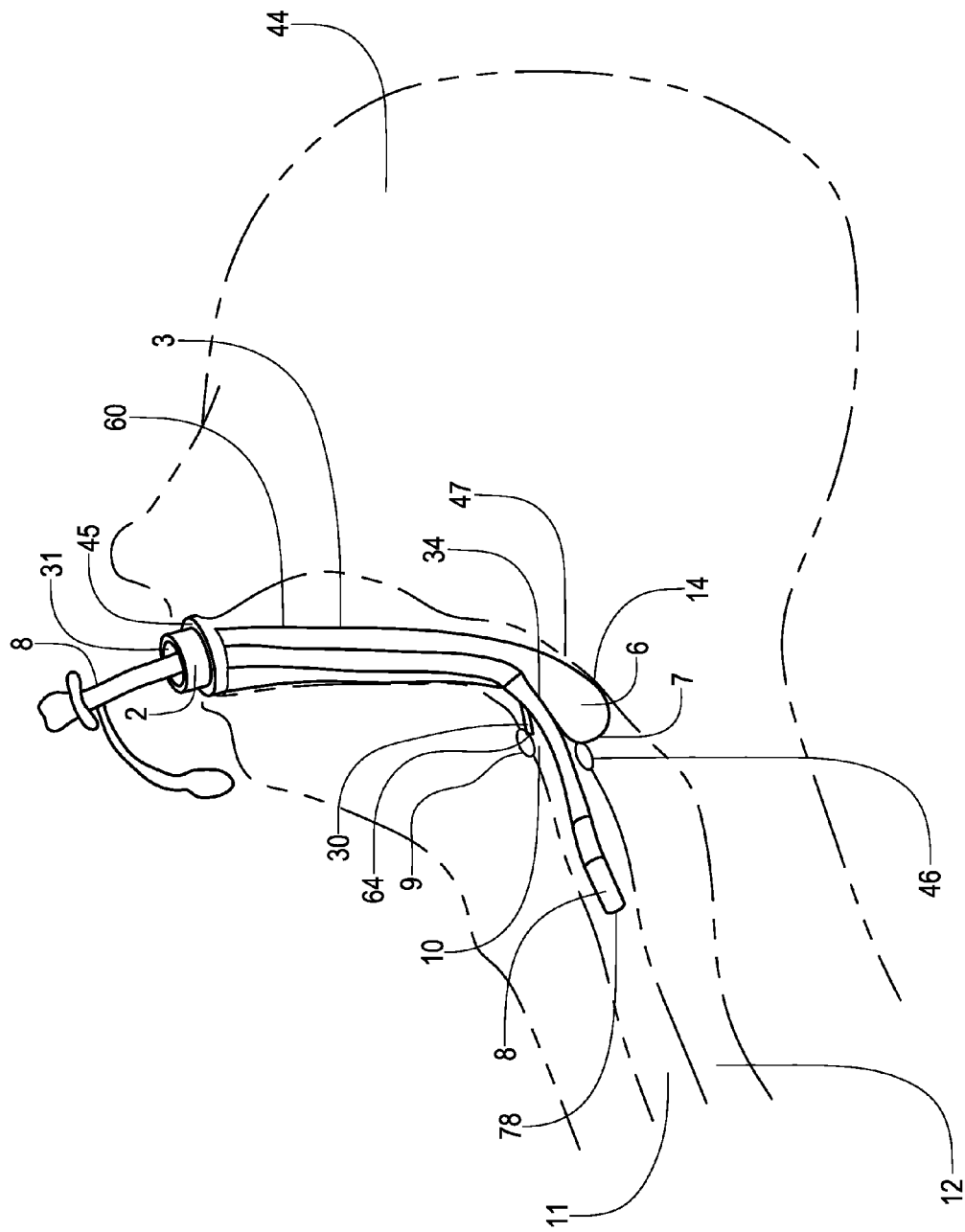
FIG. 10 provides a view of the exemplary airway device shown in FIG. 6 positioned within a patient during an endotracheal intubation procedure.

As shown in FIG. 6, distal end 6 of exemplary airway device 60 has an overall distal end width, $d_W$, bound by opposing side walls 16 and 17. As shown in FIG. 7, distal end 6 of exemplary airway device 60 has an overall distal end height, $d_H$, bound by uppermost distal end surface 13 and lower distal end surface 14, and a tear-drop shape represented by uppermost distal end surface 13, lower distal end surface 14, and a curved distal end surface 15 connecting uppermost distal end surface 13 to lower distal end surface 14. (The intersection of uppermost distal end surface 13 and curved distal end surface 15 being depicted as junction 76.) Desirably, curved distal end surface 15 extends substantially perpendicular to and between opposing side walls 16 and 17 (see, FIG. 6). Similar to exemplary airway device 50 discussed above, the tear-drop shape and outer dimensions of exemplary airway device 60 enable quick insertion of exemplary airway device 60 into a patient's mouth until curved distal end surface 15 of exemplary airway device 60 abuts corniculate cartilage of a patient (as shown in FIG. 10).

FIG. 7 provides a side view of exemplary airway device 60 shown in FIG. 6. As shown in FIG. 7, exemplary airway device 60 desirably has a curved configuration. The curved configuration may be further described with reference to lines 20-20 and 21-21, as well as angle A (i.e., angle of curvature) formed therebetween. In one desired embodiment, tubular member 61 has a curved section between proximal end 1 and distal end 6 such that (i) a first line 21-21 extending substantially parallel to tubular member 61 out of first channel opening 35 (i.e., dissects first channel opening 35) and (ii) a second line 20-20 extending from distal end 6 through curved distal end surface 15 and positioned an equal distance from uppermost distal end surface 13 and lower distal end surface 14 forms an angle A with one another of less than 180°. Typically, angle A ranges from about 110° to about 165°, more typically, from about 130° to about 145°, and in one exemplary embodiment, about 140°.

FIG. 8 provides a cross-sectional view of exemplary airway device 60 shown in FIG. 6 along line B-B shown in FIG. 6. As shown in FIG. 8, channel 31 extends from first channel opening 35 along tubular member 61 through second channel opening 34 to end point 33. As shown in FIG. 8, first channel opening 35 may have an opening inner diameter slightly larger than an inner diameter of tubular conduit 3.

Further, as shown in FIG. 8, distal end 6 of exemplary airway device 60 desirably provides an upward surface inclination from second channel opening 34 to a point along uppermost distal end surface 13. In one desired embodiment, channel 31 has a lowest channel point 32 along channel 31, wherein lowest channel point 32 is a first distance $d_2$ above lower distal end surface 14, and channel 31 has a highest channel point at end point 33 along uppermost distal end surface 13 or curved distal end surface 15, wherein end point 33 is a second distance $d_3$ above lower distal end surface 14, wherein second distance $d_3$ is greater than first distance $d_2$.

This feature of exemplary airway device 60 may be further described with reference to lines 84-84 and 85-85, as well as angle C (also referred to herein as the "angle of inclination") formed therebetween. In one desired embodiment, distal end 6 of exemplary airway device 60 provides an upward surface inclination such that (i) first line 85-85 extending substantially parallel to lower distal end surface 14 and (ii) line 84-84 extending through lowest channel point 32 and through end point 33 forms an angle C with one another of greater than about 10°. Typically, angle C ranges from about 10° to about 60°, more typically, from about 25° to about 50°, and in one exemplary embodiment, about 30° to about 40°.

As shown in FIG. 8 and discussed above, second end 64 of epiglottis guard 30 is operatively adapted to move into or away from channel 31 as designated by up and down arrows F. As discussed further below with reference to FIG. 10, epiglottis guard 30 prevents the epiglottis of a patient from blocking the glottic opening during an endotracheal intubation procedure.

Figure 9:
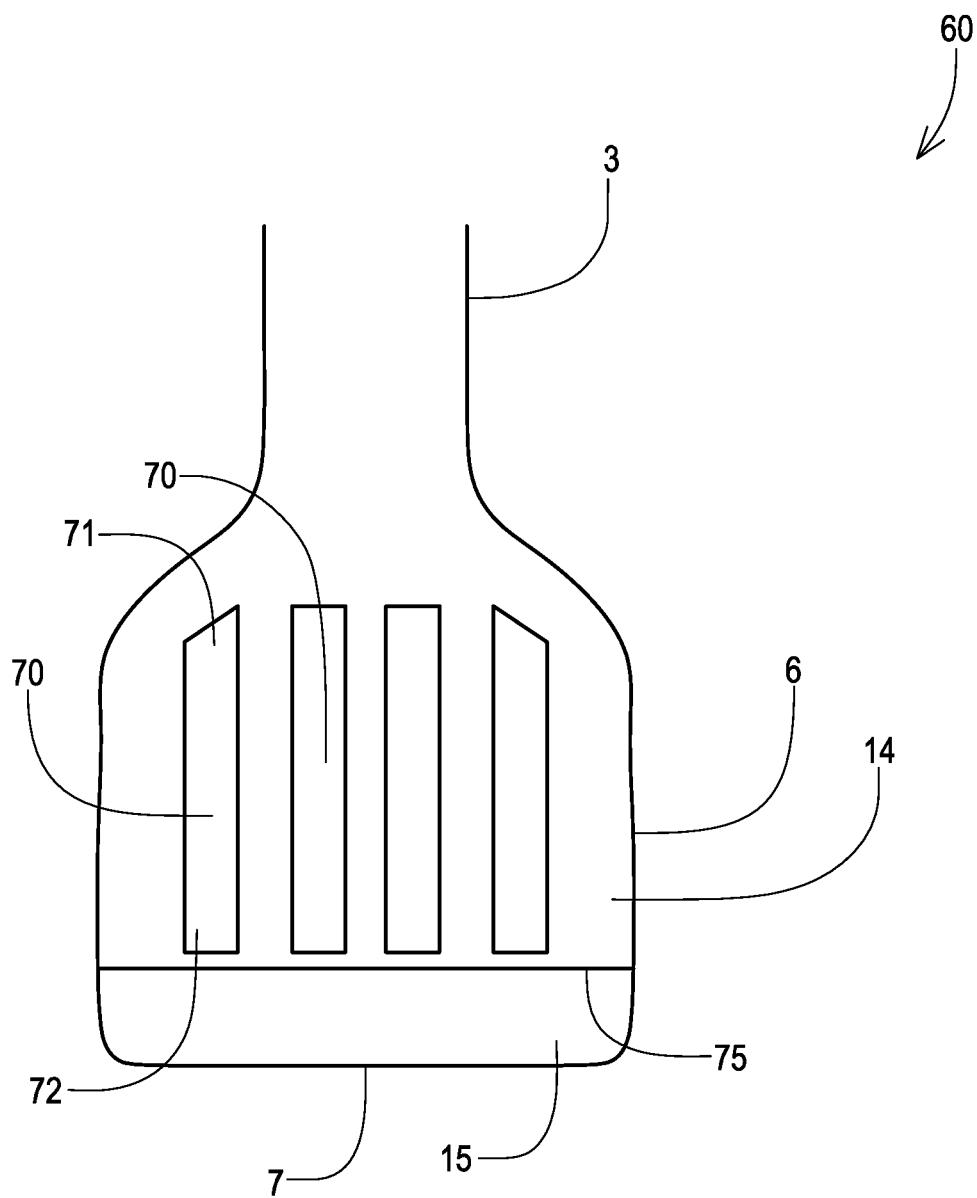
FIG. 9 provides a rear view of a distal end of the exemplary airway device shown in FIG. 6.

FIG. 9 provides a rear view of distal end 6 of exemplary airway device 60 shown in FIG. 6. As shown in FIG. 9, lower distal end surface 14 may have one or more fluid distribution channels 70 extending along a length of lower distal end surface 14. Typically, fluid distribution channels 70 are oriented so as to extend from a location proximate second channel opening 34 to a location proximate a junction 75 between lower distal end surface 14 and curved distal end surface 15. Each of fluid distribution channels 70 may have dimensions that vary depending on the outer dimensions of distal end 6. A depth of a given fluid distribution channel 70 (i.e., the dimension extending into the page) may be constant along a length of fluid distribution channel 70 or may vary along a length of fluid distribution channel 70. In one exemplary embodiment, the depth of each of the fluid distribution channels 70 increases from location 71 to location 72 within a given fluid distribution channel 70 so as to follow along the inclination angle of channel 31 (e.g., angle C shown in FIG. 8). In another exemplary embodiment, the depth of each of the fluid distribution channels 70 is substantially the same from location 71 to location 72 within a given fluid distribution channel 70.

It should be understood that fluid distribution channels 70 are one optional feature for distal end 6 of exemplary airway device 50 and/or 60, and are not required. The presence of fluid distribution channels 70 may provide one or more advantages (i) to the resulting device (e.g., enhanced structural stability at the distal end), (ii) during use (e.g., enhanced fluid flow within a patient's throat), as well as (iii) during manufacturing (e.g., reduces mold element thickness of any given portion of the distal end using an injection molding step).

FIG. 10 provides a view of exemplary airway device 60 in combination with endotracheal tube 8 as positioned within a patient 44 during an endotracheal intubation procedure. As shown in FIG. 10, exemplary airway device 60 extends from out of mouth 45 of patient 44 to corniculate cartilage 46 proximate the opening into the esophagus 12 of patient 44. Distal end tip 7 of distal end 6 abuts corniculate cartilage 46 so as to position second channel opening 34 and epiglottis guard 30 proximate glottic opening 10 leading into the trachea 11 of patient 44. Overall distal end height, $d_H$, of distal end 6 prevents exemplary airway device 60 from extending beyond corniculate cartilage 46 and into esophagus 12. (Note that lower distal end surface 14 is in contact with throat wall 47 so as to lodge distal end 6 against corniculate cartilage 46.) Endotracheal tube 8 extends through channel 31 of exemplary airway device 60, out of second channel opening 34, along channel 31 and along uppermost distal end surface 13, through glottic opening 10 and into trachea 11 of patient 44.

As shown in FIG. 10, epiglottis guard 30 of exemplary airway device 60 comes into contact with epiglottis 9 when endotracheal tube 8 extends out of second channel opening 34. As leading end 78 of endotracheal tube 8 moves out of second channel opening 34 and along uppermost distal end surface 13, the outer dimensions of endotracheal tube 8 exert an upward force on second end 64 of epiglottis guard 30, causing second end 64 of epiglottis guard 30 to push epiglottis 9 out of glottic opening 10 so that leading end 78 of endotracheal tube 8 can move into trachea 11 of patient 44 without obstruction.

The above-described airway devices are desirably free from any inflatable components. In other words, the disclosed airway devices comprise a rigid structure that is not inflatable. Further, the disclosed airway devices are typically free from any voids or empty spaces other than the above-described channel (e.g., channel 31) and the above-described optional fluid distribution channels (e.g., fluid distribution channels 70).

In addition, the above-described tear-drop shape represented by the uppermost distal end surface, the lower distal end surface, and the curved distal end surface connecting the uppermost distal end surface to the lower distal end surface is described as having a curved distal end surface that extends substantially perpendicular to and between the opposing side walls. It should be noted that the curved distal end surface desirably extends substantially perpendicular to and between the opposing side walls continuously along an outer periphery of each of the opposing side walls. In other words, the distal end typically does not contain any voids or empty space between the opposing side walls and along the curved distal end surface except possibly a portion of channel 31. Further, the distal end tip (e.g., tip 7) positioned along the distal end (e.g., distal end 6) does not comprise any further extensions beyond curved distal end surface (e.g., curved distal end surface 15). In other words, curved distal end surface forms an outermost portion of the distal end tip.

Although the above-described airway devices may have any desired dimensions, typically the above-described airway devices have dimensions as shown in the table below.

| Dimension | Typical Range | More Typical Range |
|---|---|---|
| overall length | about 10.2 cm (4.0 in) to about 20.3 cm (8.0 in) | about 12.7 cm (5.0 in) to about 17.8 cm (7.0 in) |
| distal end width, $d_W$ | about 2.5 cm (1.0 in) to about 7.6 cm (3.0 in) | about 3.2 cm (1.25 in) to about 3.8 cm (1.5 in) |
| distal end height, $d_H$ | about 1.3 cm (0.5 in) to about 3.8 cm (1.5 in) | about 1.9 cm (0.75 in) to about 2.5 cm (1.0 in) |
| channel inner diameter | about 1.3 cm (0.5 in) to about 3.8 cm (1.5 in) | about 1.3 cm (0.5 in) to about 1.9 cm (0.75 in) |
| tubular conduit outer diameter | about 1.9 cm (0.75 in) to about 5.1 cm (2.0 in) | about 1.9 cm (0.75 in) to about 2.5 cm (1.0 in) |
| length of depth indicator ring | about 0.8 cm (0.3 in) to about 2.5 cm (1.0 in) | about 0.8 cm (0.3 in) to about 1.3 cm (0.5 in) |
| tubular conduit wall thickness | about 0.25 cm (0.10 in) to about 0.63 cm (0.25 in) | about 0.25 cm (0.10 in) to about 0.51 cm (0.20 in) |
| wall thickness of depth indicator ring | about 0.25 cm (0.10 in) to about 0.95 cm (0.375 in) | about 0.51 cm (0.20 in) to about 0.8 cm (0.3 in) |
| length of epiglottis guard | about 1.3 cm (0.5 in) to about 6.3 cm (2.5 in) | about 1.9 cm (0.75 in) to about 3.8 cm (1.5 in) |
| angle of curvature along device (e.g., angle A shown in FIGS. 2 and 7) | about 110° to about 170° | about 130° to about 150° |
| angle of channel inclination (e.g., angle B shown in FIG. 2 and angle C shown in FIG. 8) | about 20° to about 60° | about 20° to about 40° |

Figure 11:
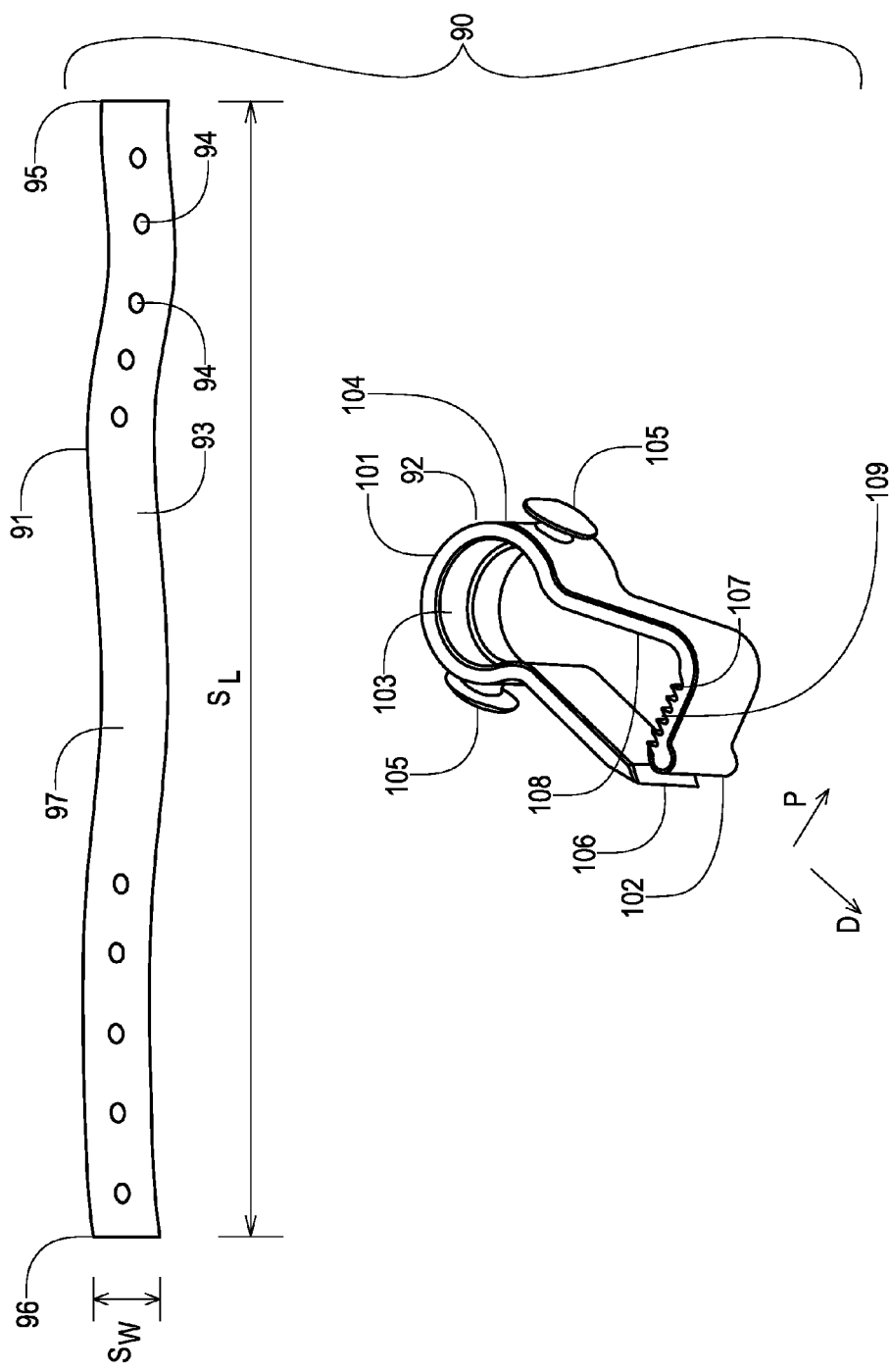
FIG. 11 provides a view of an exemplary tube securing device of the present invention.

The present invention is further directed to tube securing devices that are capable of securing an endotracheal tube to a patient. FIG. 11 provides a view of an exemplary tube securing device 90 of the present invention. As shown in FIG. 11, exemplary tube securing device 90 comprises (1) an endotracheal tube clamping member 92 operatively adapted to clamp onto an outer surface of an endotracheal tube (not shown; see, for example, exemplary endotracheal tube 8 in FIGS. 4-5 and 10), and (2) a strap 91. Endotracheal tube clamping member 92 comprising at least one clamp connector 105 positioned along an outer surface 104 of endotracheal tube clamping member 92. Strap 91 comprising one or more strap connectors 94 positioned along a length $S_L$ of strap 91, wherein each of the one or more strap connectors 94 are independently connectable to a corresponding clamp connector 105 (e.g., a single corresponding clamp connector 105 or multiple corresponding clamp connectors 105).

As shown in FIG. 11, exemplary endotracheal tube clamping member 92 comprises a closed end 101 having a closed end inner surface 103 and a closed end outer surface 104, an open end 102 opposite closed end 104 and comprising a pawling member 106 and a ratcheting member 107. Ratcheting member 107 comprises a row of ratcheting teeth 109 along an inner surface 108 of ratcheting member 107. Pawling member 106 is movable in a direction (as shown by arrow P) so as to engage with row of ratcheting teeth 109 along an inner surface 108 of ratcheting member 107 and lock pawling member 106 at a position along row of ratcheting teeth 109. As pawling member 106 moves further in the P direction, exemplary endotracheal tube clamping member 92 clamps onto an outer surface of an endotracheal tube (not shown) positioned along inner surface 103 of closed end 101.

To disengage exemplary endotracheal tube clamping member 92 from an endotracheal tube (not shown) positioned along inner surface 103 of closed end 101, a user forces ratcheting member 107 outward (e.g., in a direction shown by arrow D) so as to enable pawling member 106 to disengage with row of ratcheting teeth 109 and move in a direction opposite the P direction. Once pawling member 106 is disengaged from row of ratcheting teeth 109, exemplary endotracheal tube clamping member 92 can be removed from the endotracheal tube (not shown).

As discussed above, the endotracheal tube clamping member of the present invention may comprise comprising at least one clamp connector (e.g., clamp connector 105). As shown in FIG. 11, exemplary endotracheal tube clamping member 92 comprises a pair of clamp connectors 105 positioned along opposite sides of closed end outer surface 104. Although each clamp connector 105 may have any connector configuration that enables connection with a corresponding strap connector, in one desired embodiment, each clamp connector 105 comprises a mushroom-shaped member extending outward from opposite sides of closed end outer surface 104 as shown in FIG. 11. As used herein, the term "mushroom-shaped member" is used to describe a connector member comprising (i) an outermost shaped member and a stem portion connecting the outermost shaped member to a surface (e.g., closed end outer surface 104), wherein the outermost shaped member has a cross-sectional area extending substantially parallel with the surface (e.g., closed end outer surface 104) that is greater than a cross-sectional area of the stem portion.

Endotracheal tube clamping members used in the tube securing devices of the present invention (e.g., exemplary endotracheal tube clamping member 92) may be formed using a variety of materials. Suitable materials include, but are not limited to, polymeric materials such as polyester, polypropylene, and polyvinyl chloride. In one desired embodiment, the endotracheal tube clamping member used in the tube securing devices of the present invention is formed using polypropylene.

As shown in FIG. 11, strap 91 comprising a strip of material 93 having opposite strip ends 95 and 96, a strip width $S_W$, a strip length $S_L$ extending between opposite strip ends 95 and 96, and a plurality of strap connectors 94 positioned along strip length $S_L$. Typically, strip length $S_L$ is about 10 or more (or about 15, or about 20, or about 25, or about 30) times greater than strip width $S_W$. In one exemplary embodiment, strip width $S_W$ ranges from about 0.5 cm (0.2 in) to about 5.1 cm (2.0 in) (or from about 1.3 cm (0.5 in) to about 2.5 cm (1.0 in)), and strip length $S_L$ ranges from about 25 cm (10 in) to about 75 cm (29.5 in) (or from about 38.1 cm (15 in) to about 63.5 cm (25 in)). In one desired embodiment, strip width $S_W$ is about 1.9 cm (0.75 in), and strip length $S_L$ is about 55.2 cm (21.75 in).

As with the clamp connectors discussed above, each strap connector may have any connector configuration that enables connection with a corresponding clamp connector. In one desired embodiment, each strap connector 94 comprises an opening extending through strap 91, wherein each opening is dimensioned so as to fit over and engage with at least one clamp connector, such as exemplary clamp connectors 105 having a configuration in the form of mushroom-shaped members.

Although not shown in the figures, it should be understood that clamp connectors and strap connectors may have any configuration as long as the clamp connectors and strap connectors engage with one another. For example, in an alternative embodiment, clamp connectors may comprise an opening within and/or through a surface of an endotracheal tube clamping member (e.g., an opening within and/or through outer surface 104 of endotracheal tube clamping member 92) and strap connectors may comprise a plurality of connectors in the form of mushroom-shaped members extending outward from an outer surface of the strap (e.g., extending outward from outer surface 97 of strip material 93 of strap 91).

Straps used in the tube securing devices of the present invention (e.g., strap 91) may be formed using a variety of materials. Suitable materials include, but are not limited to, polymeric materials such as ethylene-propylene copolymers, polyurethanes, and elastomeric polymers, as well as elastomeric materials such as natural and synthetic rubber materials. In one desired embodiment, the strap used in the tube securing devices of the present invention is formed using synthetic rubber material.

The present invention is further directed to methods of making airway devices and tube securing devices suitable for use in an endotracheal intubation procedure. In one exemplary embodiment, the present invention is directed to a method of making an airway device (e.g., exemplary airway device 50 or 60) comprising forming a tubular member 51 or 61 having a proximal end 1, a distal end 6 opposite proximal end 1, a tubular conduit 3 positioned between proximal end 1 and distal end 6, and a channel 31 extending from a first channel opening 35 at proximal end 1 through tubular conduit 3 to a second channel opening 34 proximate distal end 6, wherein distal end 6 of device 50 or 60 has an overall distal end width, $d_W$, bound by opposing side walls 16 and 17, an overall distal end height, $d_H$, bound by an uppermost distal end surface 13 and a lower distal end surface 14, and a tear-drop shape represented by uppermost distal end surface 13, lower distal end surface 14, and a curved distal end surface 15 connecting uppermost distal end surface 13 to lower distal end surface 14, wherein curved distal end surface 15 extends substantially perpendicular to and between opposing side walls 16 and 17.

In one exemplary embodiment, the forming step comprises a single thermoforming step (e.g., a single injection molding step), wherein thermoformable material is placed into the mold (e.g., injected) and molded to form an airway device (e.g., exemplary airway device 50 or 60). Suitable thermoformable materials for forming the disclosed airway devices include, but are not limited to, polyvinyl chlorides and polyurethanes. In one desired embodiment, the thermoformable material used to form the disclosed airway devices comprises a medical grade polyvinyl chloride.

The method of making an airway device may further comprise one or more additional steps in addition to the thermoforming step. Suitable additional method steps may include, but are not limited to, removing the molded object (e.g., the airway device) from a mold, trimming any excess material from the airway device, coating the airway device with a finish on any outer surface (e.g., coating at least a portion of channel 31 surface with a lubricant or slip agent), and forming a kit containing the airway device and at least one other kit component. Desirably, the method of making an airway device comprises a single thermoforming step (e.g., injection molding) without ant additional steps other than packaging the resulting device.

In a further exemplary embodiment, the method of making an airway device (e.g., exemplary airway device 60) comprises forming a tubular member 61 having a proximal end 1, a distal end 6 opposite proximal end 1, a tubular conduit 3 positioned between proximal end 1 and distal end 6, a channel 31 extending from a first channel opening 35 at proximal end 1 through tubular conduit 3 to a second channel opening 34 proximate distal end 6, and an epiglottis guard 30 extending along an upper portion 62 of tubular member 60. In this exemplary embodiment, the forming step may comprise a single thermoforming step (e.g., a single injection molding step as described above) or may comprise a thermoforming step (e.g., for forming tubular member 61) in combination with one or more other method steps. For example, epiglottis guard 30 may be formed by (i) a single molding step or (ii) in a separate step comprising cutting upper portion 62 of tubular member 61 extending over channel 31 so as to form epiglottis guard 30 comprising (i) first end 63 that is connected to tubular member 61 proximate second channel opening 34, (ii) second end 64 that is not connected to tubular member 61 and is positioned between second channel opening 34 and distal end 6, and (iii) opposing cut edges 65 and 66 extending from second end 64 to first end 63, wherein second end 64 of epiglottis guard 30 is operatively adapted to move into or away from channel 31, for example, during insertion of endotracheal tube 8 through channel 31 of device 60 and into a patient's trachea 11.

In any of the above-described methods of forming an airway device, a single thermoforming step (e.g., molding step) may be used to form one or more fluid distribution channels 70 along lower distal end surface 14 as described above. Any of the above-mentioned additional steps (other than the thermoforming step) may be used to further provide one or more features to the resulting airway device.

The present invention is also directed to methods of making any of the above-described tube securing devices (e.g., exemplary tube securing device 90). In one exemplary embodiment, the method of making a tube securing device (e.g., exemplary tube securing device 90) comprises (i) forming an endotracheal tube clamping member (e.g., exemplary endotracheal tube clamping member 92), wherein the endotracheal tube clamping member comprising at least one clamp connector (e.g., exemplary clamp connector 105) positioned along an outer surface of the endotracheal tube clamping member; and (ii) forming a strap (e.g., exemplary strap 91) comprising one or more strap connectors (e.g., exemplary strap connectors 94) positioned along a length of the strap, wherein each of the one or more strap connectors are independently connectable to a corresponding clamp connector (e.g., exemplary clamp connector 105).

In one exemplary embodiment, the step of forming an endotracheal tube clamping member (e.g., exemplary endotracheal tube clamping member 92) comprises a single thermoforming step (e.g., a single injection molding step), wherein thermoformable material is placed into the mold (e.g., injected) and molded to form an endotracheal tube clamping member (e.g., exemplary endotracheal tube clamping member 92). As discussed above, thermoformable materials suitable for forming the disclosed endotracheal tube clamping member include, but are not limited to, polymeric materials such as polyester, polypropylene, and polyvinyl chloride. In one desired embodiment, the thermoformable material used to form the disclosed endotracheal tube clamping member comprises polypropylene.

In one exemplary embodiment, the step of forming a strap (e.g., exemplary strap 91) comprises a single thermoforming step (e.g., a single extrusion step), wherein thermoformable material is extruded through a die to form a sheet of strap material. As discussed above, thermoformable materials suitable for forming the disclosed strap include, but are not limited to, polymeric materials such as ethylene-propylene copolymers, polyurethanes, and elastomeric polymers, as well as elastomeric materials such as natural and synthetic rubber materials. In one desired embodiment, the thermoformable material used to form the disclosed strap comprises synthetic rubber material.

The method of making an endotracheal tube clamping member (e.g., exemplary endotracheal tube clamping member 92) and/or a strap (e.g., exemplary strap 91) may further comprise one or more additional steps in addition to one or more thermoforming steps. Suitable additional method steps may include, but are not limited to, removing the molded object (e.g., exemplary endotracheal tube clamping member 92) from a mold, trimming any excess material from the endotracheal tube clamping member or strap, coating the endotracheal tube clamping member or strap with a finish on any outer surface (e.g., coating at least a portion of inner surface 103 with an anti-slip agent), slitting an extruded sheet of strap material into strips of strap material having a desired strap width ($S_W$) and strap length ($S_L$), punching one or more openings into an outer surface of the endotracheal tube clamping member or strap, permanently fixing (e.g., via a single molding step) or temporarily fixing (e.g., via a connection step) one end of the strap to the endotracheal tube clamping member, and forming a kit containing an endotracheal tube clamping member (e.g., exemplary endotracheal tube clamping member 92) and a strap (e.g., exemplary strap 91) in combination with an airway device, an endotracheal tube, a combination of an airway device and an endotracheal tube, and any other kit component (e.g., a lubricant).

The present invention is further directed to methods of using the above-described airway devices (e.g., exemplary airway device 50 or 60) and tube securing devices (e.g., exemplary tube securing device 90) in an endotracheal intubation procedure. In one exemplary embodiment, the method of inserting an endotracheal tube 8 into a trachea 11 of a patient 44 comprises the steps of inserting an airway device (e.g., exemplary airway device 50 or 60) into the patient's mouth 45 until a curved distal end surface 15 of the device abuts corniculate cartilage 46 of the patient 44, wherein (1) the device comprises a tubular member 51 or 61 having a proximal end 1, a distal end 6 opposite proximal end 1, a tubular conduit 3 positioned between proximal end 1 and distal end 6, and a channel 31 extending from a first channel opening 35 at proximal end 1 through tubular conduit 3 to a second channel opening 34 proximate distal end 6, (2) distal end 6 has an overall distal end width, $d_W$, bound by opposing side walls 16 and 17, an overall distal end height, $d_H$, bound by an uppermost distal end surface 13 and a lower distal end surface 14, and a tear-drop shape represented by uppermost distal end surface 13, lower distal end surface 14, and curved distal end surface 15 connecting uppermost distal end surface 13 to lower distal end surface 14, and (3) curved distal end surface 15 extends substantially perpendicular to and between opposing side walls 16 and 17; and pushing endotracheal tube 8 through channel 31 of the device.

The exemplary method of using the above-described airway devices may comprise one or more additional steps including, but not limited to, connecting a ventilation mask (not shown) to the proximal end 1 of the device after the inserting step; disconnecting the ventilation mask from the proximal end 1 of the device after the connecting step and prior to the pushing step; coating at least a portion of a leading end 78 of endotracheal tube 8 with a lubricant (not shown) prior to the pushing step; and any combination of the above-mentioned steps.

In some embodiments of the present invention, the methods of using one of the above-described airway devices further comprise a step of securing a portion of an endotracheal tube extending from a patient's mouth to the patient via one of the above-described tube securing devices of the present invention. An exemplary combination of an airway device, an endotracheal tube, and a tube securing device suitable for use in such a method is shown in FIG. 12.

Figure 12:
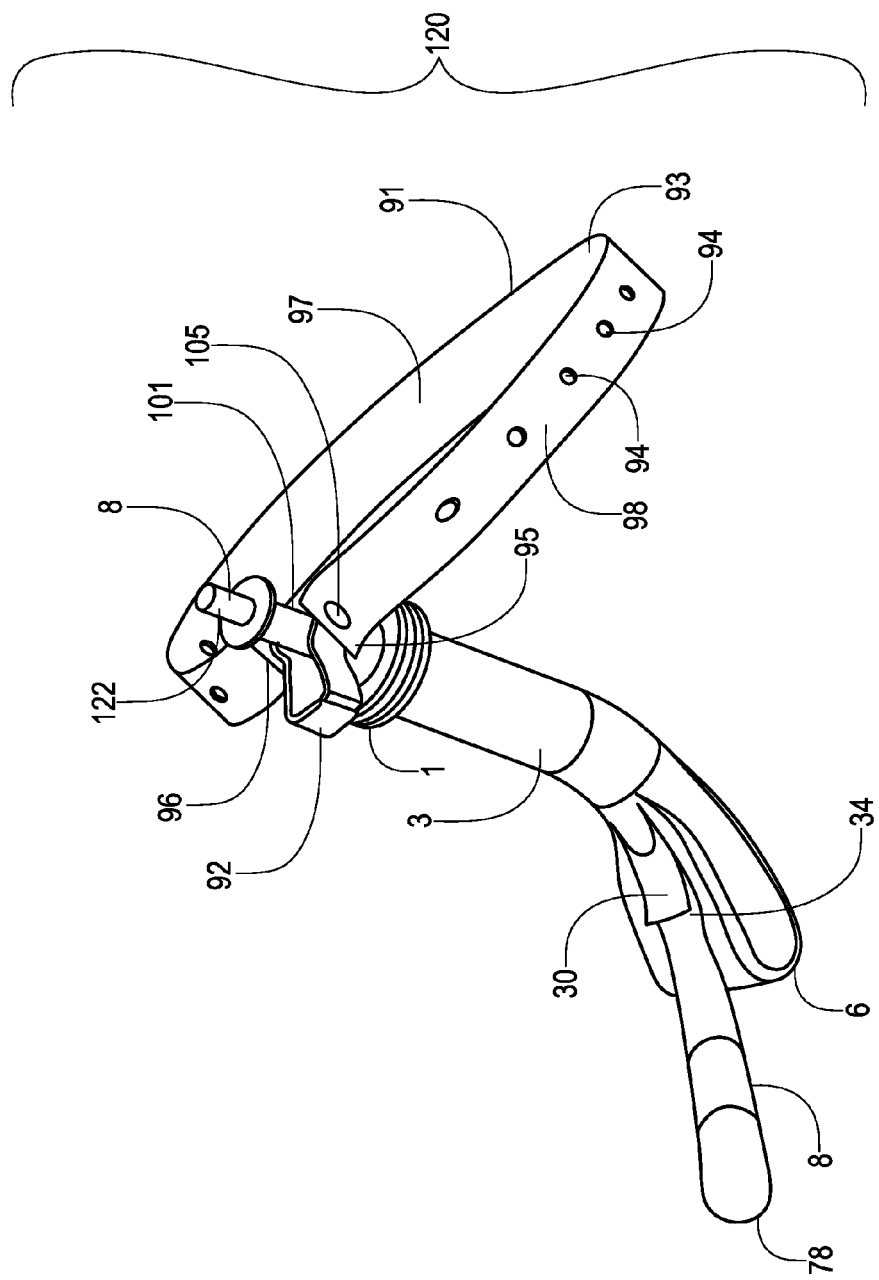
FIG. 12 provides a view of the exemplary tube securing device shown in FIG. 11 in combination with an endotracheal tube positioned within the exemplary airway device shown in FIG. 6.

As shown in FIG. 12, exemplary combination 120 comprises exemplary tube securing device 90 (as shown in FIG. 11) in combination with endotracheal tube 8 positioned within exemplary airway device 3 (as shown in FIG. 6). In exemplary combination 120, endotracheal tube 8 extends through exemplary airway device 3 such that leading end 78 of endotracheal tube 8 extends out of second channel opening 34 at distal end 6, forcing upward epiglottis guard 30. An opposite end 122 of endotracheal tube 8 extends from proximate end 1 of exemplary airway device 3. Exemplary tube securing device 90 is shown attached to a portion of endotracheal tube 8 proximate opposite end 122 with exemplary endotracheal tube clamping member 92 of exemplary tube securing device 90 clamped onto endotracheal tube 8 and exemplary strap 91 of exemplary tube securing device 90 attached to exemplary clamp connectors 105 positioned on opposite sides of exemplary endotracheal tube clamping member 92. As shown in FIG. 12, unused strap connectors 94 extend along a length ($S_L$) of strap 91 and through strip material 93 from first outer surface 98 to second (i.e., opposite) outer surface 97.

The present invention is further directed to a method of stabilizing a position of an endotracheal tube inserted into a trachea of a patient using a combination such as exemplary combination 120. In one exemplary embodiment, the method comprises positioning an endotracheal tube clamping member (e.g., exemplary endotracheal tube clamping member 92) of a tube securing device (e.g., exemplary tube securing device 90) around a portion of an outer surface of an endotracheal tube (e.g., exemplary endotracheal tube 8) extending out of a patient's mouth so as to surround the portion of the endotracheal tube; clamping the endotracheal tube clamping member onto the portion of the endotracheal tube (e.g., via forcing pawling member 106 of exemplary endotracheal tube clamping member 92 onto row of teeth 109 as discussed above); and attaching at least one strap connector (e.g., strap connector 94) of a strap of the tube securing device (e.g., strap 91) to at least one corresponding clamp connector (e.g., clamp connector 105) on the endotracheal tube clamping member (e.g., exemplary endotracheal tube clamping member 92) so as to surround a portion of the patient's head and stabilize a position of the endotracheal tube relative to the patient. Such a method is depicted in FIG. 13.

Figure 13:
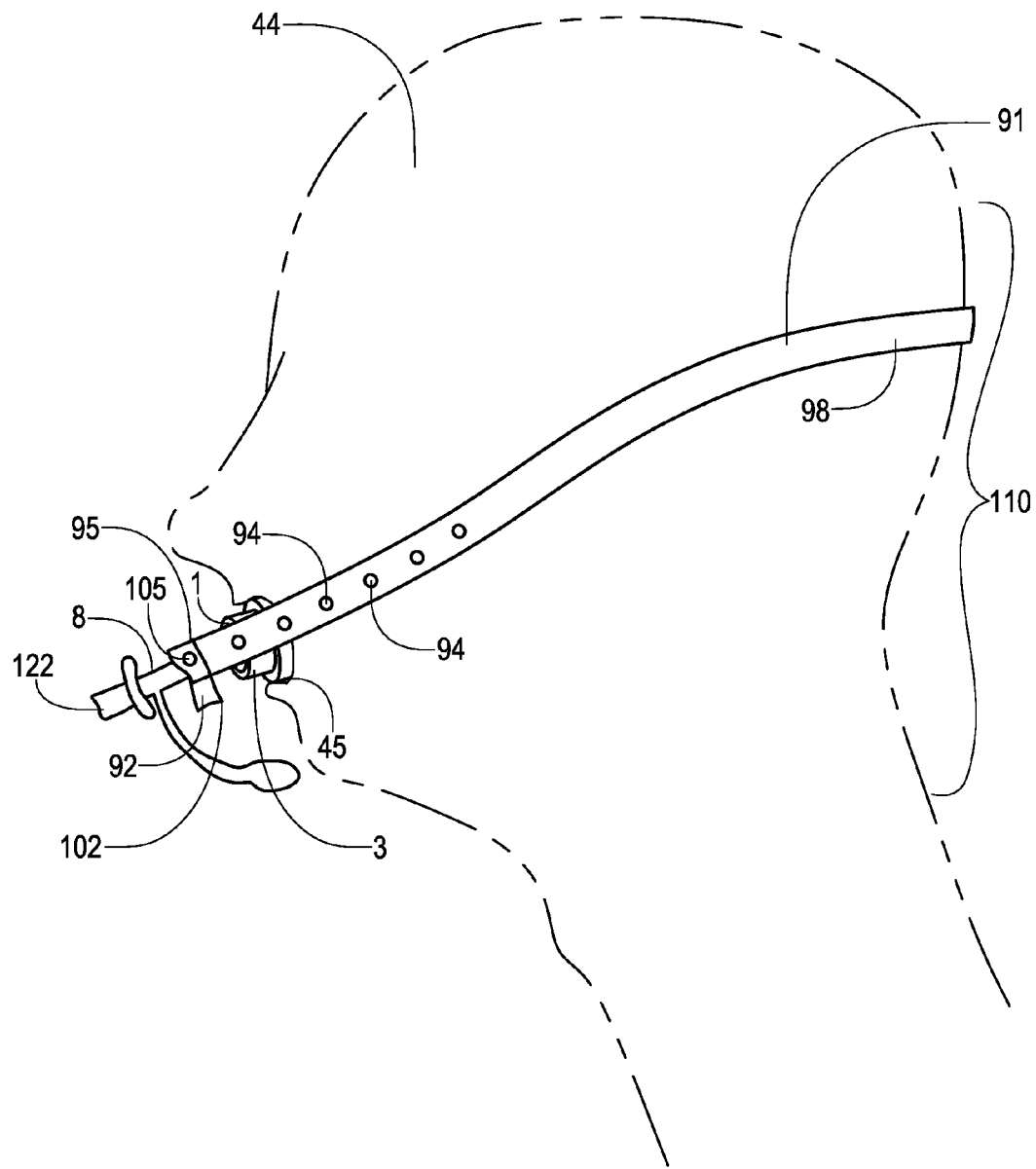
FIG. 13 provides a view of the exemplary tube securing device and airway device combination shown in FIG. 12 in use on a patient.

As shown in FIG. 13, opposite end 122 of endotracheal tube 8 extends out of proximate end 1 of exemplary airway device 3, both of which extends out of the mouth 45 of patient 44. Exemplary endotracheal tube clamping member 92 of exemplary tube securing device 90 is shown clamped onto endotracheal tube 8 while exemplary strap 91 of exemplary tube securing device 90 is shown attached to exemplary clamp connectors 105 positioned on opposite sides of exemplary endotracheal tube clamping member 92 and extending around a portion of patient 44 (i.e., the head and/or neck region of patient 44). Exemplary strap 91 may be positioned so as to contact patient 44 along a rear head/neck region 110 as shown in FIG. 13.

The above exemplary method of stabilizing a position of an endotracheal tube inserted into a trachea of a patient may comprise attaching a first strap connector (e.g., exemplary strap connector 94) of the strap (e.g., exemplary strap 91) to a first corresponding clamp connector (e.g., exemplary clamp connector 105) on the endotracheal tube clamping member (e.g., exemplary endotracheal tube clamping member 92) prior to the positioning step (i.e., the step of positioning an endotracheal tube clamping member (e.g., exemplary endotracheal tube clamping member 92) of a tube securing device (e.g., exemplary tube securing device 90) around a portion of an outer surface of an endotracheal tube (e.g., exemplary endotracheal tube 8) extending out of a patient's mouth so as to surround the portion of the endotracheal tube). The above exemplary method of stabilizing a position of an endotracheal tube inserted into a trachea of a patient may further comprise attaching a second strap connector (e.g., exemplary strap connector 94) of the strap (e.g., exemplary strap 91) to a second corresponding clamp connector (e.g., exemplary clamp connector 105) on the endotracheal tube clamping member (e.g., exemplary endotracheal tube clamping member 92) after the clamping step (e.g., the step of clamping the endotracheal tube clamping member onto the portion of the endotracheal tube) so as to surround the portion of the patient's head and stabilize the position of the endotracheal tube relative to the patient. Further, the positioning step and the clamping step may occur prior to a step of inserting the endotracheal tube into the trachea of the patient.

The above-described airway devices and tube securing devices may each be provided as an individual component or as one component in a kit for performing an endotracheal intubation procedure. One exemplary kit comprises at least one of the above-described airway devices in combination with an endotracheal tube. Another exemplary kit comprises the above-described tube securing device in combination with an endotracheal tube. A further exemplary kit comprises the above-described tube securing device in combination with at least one of the above-described airway devices. Yet a further exemplary kit comprises the above-described tube securing device in combination with at least one of the above-described airway devices and an endotracheal tube. Another exemplary kit comprises kit components including, but not limited to, at least one of the above-described airway devices, at least one of the above-described tube securing devices, an endotracheal tube, a lubricant, a ventilation mask, or any combination thereof.

In one exemplary embodiment, a given kit comprises at least one of the above-described tube securing devices in combination with an airway device, wherein the airway device comprises a tubular member having a proximal end, a distal end opposite the proximal end, a tubular conduit positioned between the proximal end and the distal end, and a channel extending from a first channel opening at the proximal end through the tubular conduit to a second channel opening proximate the distal end; the distal end having an overall distal end width bound by opposing side walls, an overall distal end height bound by an uppermost distal end surface and a lower distal end surface, and a tear-drop shape represented by the uppermost distal end surface, the lower distal end surface, and a curved distal end surface connecting the uppermost distal end surface to the lower distal end surface, the curved distal end surface extending substantially perpendicular to and between the opposing side walls.

In another exemplary embodiment, a given kit comprises at least one of the above-described tube securing devices in combination with an airway device, wherein the airway device comprises a tubular member having a proximal end, a distal end opposite the proximal end, a tubular conduit positioned between the proximal end and the distal end, and a channel extending from a first channel opening at the proximal end through the tubular conduit to a second channel opening proximate the distal end, and an epiglottis guard extending along an upper portion of the tubular member, the epiglottis guard comprising (i) a first end that is connected to the tubular member proximate the second channel opening, (ii) a second end that is not connected to the tubular member and positioned between the second channel opening and the distal end, and (iii) opposing edges extending from the first end to the second end, the opposing edges being not connected to the tubular member, wherein the second end is operatively adapted to move into or away from the channel.

In a further exemplary embodiment, a given kit comprises a tube securing device in combination with an airway device, wherein the tube securing device comprises (1) an endotracheal tube clamping member operatively adapted to clamp onto an outer surface of an endotracheal tube, the endotracheal tube clamping member comprising (i) a closed end having a closed end inner surface and a closed end outer surface, (ii) an open end opposite the closed end and comprising (iii) a pawling member and (iv) a ratcheting member, the pawling member being movable along a row of ratcheting teeth along the ratcheting member so as to lock the pawling member within the ratcheting member and simultaneously clamp onto the outer surface of the endotracheal tube, and (v) a pair of clamp connectors positioned along opposite sides of the closed end outer surface, wherein each of the clamp connectors comprises a mushroom-shaped member extending outward from opposite sides of the closed end outer surface; and (2) a strap comprising (i) a strip of material having opposite strip ends, a strip width, and a strip length extending between the opposite strip ends, and (ii) a plurality of strap connectors positioned along the strip length, each of the one or more strap connectors being independently connectable to a corresponding clamp connector, wherein each strap connector comprises an opening extending through the strap.

The present invention is described above and further illustrated below by way of examples, which are not to be construed in any way as imposing limitations upon the scope of the invention. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

An airway device was formed via an injection molding step in which medical grade polyvinyl chloride was molded into a shape as shown in FIGS. 1-3. The resulting airway device had the following dimensions:
length=16.5 cm (6.5 in)
width of distal end=3.49 cm (1.375 in)
height of distal end=2.22 cm (0.875 in)
inner diameter=2.22 cm (0.875 in)
outer diameter=3.18 cm (1.25 in)
length of depth indicator ring=2.86 cm (1.125 in)
tubular conduit wall thickness=0.48 cm (0.1875 in)
angle of curvature along device=140°
angle of inclination along distal end of device=40°.

EXAMPLE 2

An airway device was formed via an injection molding step in which medical grade polyvinyl chloride was molded into a shape as shown in FIGS. 6-9. The resulting airway device had the following dimensions:
length=14.5 cm (5.7 in)
width of distal end=3.65 cm (1.438 in)
height of distal end=4.44 cm (1.75 in)
inner diameter=1.59 cm (0.625 in)
outer diameter=2.22 cm (0.875 in)
length of depth indicator ring=1.11 cm (0.438 in)
tubular conduit wall thickness=0.32 cm (0.125 in)
angle of curvature along device=135°
angle of inclination along distal end of device=30°
length of epiglottis guard ($g_L$)=3.18 cm (1.25 in).

EXAMPLE 3

A tube securing device was formed. An endotracheal tube clamping member (e.g., exemplary endotracheal tube clamping member 92) was formed via an injection molding step in which polypropylene was molded into a shape as shown in FIGS. 11-13. The resulting endotracheal tube clamping member had the following dimensions and features:
length=3.49 cm (1.375 in)
width of closed end=2.38 cm (0.937 in)
width of open end=1.59 cm (0.625 in)
height of member=1.11 cm (0.437 in)
inner diameter of closed end=1.11 cm (0.437 in)
outer diameter of closed end=1.59 cm (0.625 in)
length of each clamp connector=0.38 cm (0.150 in)
diameter of a given clamp connector stem portion=0.32 cm (0.125 in)
overall diameter of a given clamp connector=0.83 cm (0.325 in)
approximate number of teeth in row of teeth=9.

A strap (e.g., exemplary strap 91) was formed via an extrusion step in which synthetic rubber material was extruded into a shape as shown in FIGS. 11-13. The resulting strap had the following dimensions and features:
length=55.2 cm (21.75 in)
width=1.9 cm (0.75 in)
thickness=0.06 cm (0.025 in)
total number of strap connectors=10.

The resulting tube securing device was used in combination with the airway device of Example 1 and the airway device of Example 2 as shown in FIGS. 12-13.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:
1. A kit comprising:
(a) a tube securing device for stabilizing a position of an endotracheal tube on a patient, said tube securing device comprising:

an endotracheal tube clamping member operatively adapted to clamp onto an outer surface of an endotracheal tube, said endotracheal tube clamping member comprising at least one clamp connector positioned along an outer surface of said endotracheal tube clamping member; and a strap comprising one or more strap connectors positioned along a length of said strap, each of said one or more strap connectors being independently connectable to a corresponding clamp connector, wherein said endotracheal tube clamping member comprises a pair of clamp connectors positioned along opposite sides of said closed end outer surface; and (b) an airway device.

2. The kit of claim 1, wherein said airway device comprises:

a tubular member having a proximal end, a distal end opposite the proximal end, a tubular conduit positioned between the proximal end and the distal end, and a channel extending from a first channel opening at the proximal end through the tubular conduit to a second channel opening proximate the distal end; said distal end having an overall distal end width bound by opposing side walls, an overall distal end height bound by an uppermost distal end surface and a lower distal end surface, and a tear-drop shape represented by the uppermost distal end surface, the lower distal end surface, and a curved distal end surface connecting the uppermost distal end surface to the lower distal end surface, said curved distal end surface extending substantially perpendicular to and between said opposing side walls.

3. The kit of claim 1, wherein said airway device comprises:

a tubular member having a proximal end, a distal end opposite the proximal end, a tubular conduit positioned between the proximal end and the distal end, and a channel extending from a first channel opening at the proximal end through the tubular conduit to a second channel opening proximate the distal end; and an epiglottis guard extending along an upper portion of said tubular member, said epiglottis guard comprising (i) a first end that is connected to said tubular member proximate said second channel opening, (ii) a second end that is not connected to said tubular member and positioned between said second channel opening and said distal end, and (iii) opposing edges extending from said first end to said second end, said opposing edges being not connected to said tubular member, wherein said second end is operatively adapted to move into or away from said channel.

4. A kit comprising:

(a) a tube securing device for stabilizing a position of an endotracheal tube extending from a patient's mouth, said tube securing device comprising:

(i) an endotracheal tube clamping member operatively adapted to clamp onto an outer surface of an endotracheal tube, said endotracheal tube clamping member comprising:

a closed end having a closed end inner surface and a closed end outer surface, an open end opposite said closed end and comprising a pawling member and a ratcheting member, said pawling member being movable along a row of ratcheting teeth along said ratcheting member so as to lock said pawling member within said ratcheting member and simultaneously clamp onto the outer surface of the endotracheal tube, and a pair of clamp connectors positioned along opposite sides of said closed end outer surface, wherein each of said clamp connectors comprises a mushroom-shaped member extending outward from opposite sides of said closed end outer surface; and (ii) a strap comprising:

a strip of material having opposite strip ends, a strip width, and a strip length extending between said opposite strip ends, and a plurality of strap connectors positioned along said strip length, each of said one or more strap connectors being independently connectable to a pair of clamp connectors positioned along opposite sides of said closed end outer surface of the corresponding clamp connector, wherein each strap connector comprises an opening extending through said strap; and (c) an airway device.

5. The kit of claim 4, wherein said strip length enables said strap to extend from the patient's mouth, along a rear portion of the patient's head or neck region, and back to the patient's mouth so as to surround a portion of the patient's head.

6. The kit of claim 4, wherein said endotracheal tube clamping member is formed from polypropylene, and said strip is formed from a synthetic rubber material.

7. A method of stabilizing a position of an endotracheal tube inserted into a trachea of a patient, said method comprising:

positioning the endotracheal tube clamping member of the tube securing device of claim 1 around a portion of the outer surface of the endotracheal tube extending out of the patient's mouth so as to surround the portion of the endotracheal tube;

clamping the endotracheal tube clamping member onto the portion of the endotracheal tube; and attaching at least one of the strap connectors of the strap of the tube securing device to at least one corresponding clamp connector on the endotracheal tube clamping member so as to surround a portion of the patient's head and stabilize a position of the endotracheal tube relative to the patient.

8. The method of claim 7, further comprising:

attaching a first strap connector of said strap to a first corresponding clamp connector on said endotracheal tube clamping member prior to said positioning step; and attaching a second strap connector of said strap to a second corresponding clamp connector on said endotracheal tube clamping member after said clamping step so as to surround the portion of the patient's head and stabilize the position of the endotracheal tube relative to the patient.

* * * * *